US012790120B2

(12) United States Patent
Schneider et al.

(10) Patent No.: US 12,790,120 B2
(45) Date of Patent: Nov. 10, 2026

(54) APPARATUS AND METHODS FOR AUTOMATED PICKING OF ITEMS

(71) Applicant: Remedi Technology Holdings, LLC, Towson, MD (US)

(72) Inventors: Steven E. Schneider, Lewis Center, OH (US); Richard W. Snodgrass, Columbus, OH (US); Justin J. Clark, Kitchener (CA); Christopher J. Fisher, Kitchener (CA); Steven Hoenig, Blacklick, OH (US); Kimberly Hawkes, Columbus, PA (US); Roger J. Gerdeman, Columbus, OH (US); Wyatt Culbertson, Powell, OH (US); Thomas P. Hayes, Cambridge (CA)

(73) Assignee: Remedi Technology Holdings, LLC, Towson, MD (US)

( * ) Notice: Subject to any disclaimer, the term of this patent is extended or adjusted under 35 U.S.C. 154(b) by 156 days.

(21) Appl. No.: 18/961,286

(22) Filed: Nov. 26, 2024

(65) Prior Publication Data

US 2025/0091808 A1 Mar. 20, 2025

Related U.S. Application Data

(63) Continuation of application No. 18/189,771, filed on Mar. 24, 2023, now Pat. No. 12,168,573, which is a (Continued)

(51) Int. Cl.
*B65G 1/04* (2006.01)
*B65G 1/06* (2006.01)
(Continued)

(52) U.S. Cl.
CPC ......... *B65G 1/1376* (2013.01); *B65G 1/0471* (2013.01); *B65G 1/06* (2013.01);
(Continued)

(58) Field of Classification Search
CPC .... B65G 1/1376; B65G 1/0471; B65G 1/137; B65G 47/91; B65G 59/062; G16H 20/13; G07F 17/0092; G06F 17/00
See application file for complete search history.

(56) References Cited

U.S. PATENT DOCUMENTS 3,013,693 A 12/1961 Griner
3,247,929 A 4/1966 Langley
(Continued)

FOREIGN PATENT DOCUMENTS

EP 2 373 557 A0 1/2011
WO WO1020/065845 A1 6/2010

OTHER PUBLICATIONS

Chinese Office Action issued Aug. 20, 2013, in China Patent Application No. 200980155637.5 (with Partial English translation).
(Continued)

*Primary Examiner* — Saul Rodriguez
*Assistant Examiner* — Ashley K Romano
(74) *Attorney, Agent, or Firm* — Oblon, McClelland, Maier & Neustadt, L.L.P.

(57) ABSTRACT

An automation apparatus for dispensing groups of individually packaged products including a storage module including a first storage bin configured to slidably receive a storage tube inserted therein; a first storage tube configured to store therein a plurality of products each contained in an individual package, the first storage tube including an end cap including a release slot to allow movement of a first individual package along a direction transverse to a longitudinal axis of the first storage tube for removal of the first individual package from the storage tube, the end cap including a retention slot configured to engage with a registration pin of the first storage bin and prevent the first storage tube from sliding out of the first storage bin; and a pick device
(Continued)

configured to retrieve the first individual package from the first storage tube disposed in the end cap via the release slot.

1 Claim, 26 Drawing Sheets

Related U.S. Application Data continuation of application No. 16/984,986, filed on Aug. 4, 2020, now Pat. No. 11,649,115, which is a continuation of application No. 15/893,066, filed on Feb. 9, 2018, now Pat. No. 10,759,602, which is a continuation of application No. 14/859,778, filed on Sep. 21, 2015, now Pat. No. 9,908,704, which is a continuation of application No. 12/559,601, filed on Sep. 15, 2009, now Pat. No. 9,745,131.

(60) Provisional application No. 61/120,209, filed on Dec. 5, 2008.

(51) Int. Cl.

| | |
|---|---|
| ***B65G 1/137*** | (2006.01) |
| ***B65G 47/91*** | (2006.01) |
| ***B65G 59/06*** | (2006.01) |
| ***G06F 17/00*** | (2019.01) |
| ***G07F 17/00*** | (2006.01) |
| ***G16H 20/13*** | (2018.01) |

(52) U.S. Cl.
CPC ............. *B65G 1/137* (2013.01); *B65G 47/91* (2013.01); *B65G 59/062* (2013.01); *G06F 17/00* (2013.01); *G07F 17/0092* (2013.01); *G16H 20/13* (2018.01)

(56) References Cited

U.S. PATENT DOCUMENTS 3,308,962 A 3/1967 Bryant
3,386,558 A 6/1968 Benatar
3,503,493 A 3/1970 Joseph
3,511,395 A 5/1970 Brown, Jr.
3,527,368 A 9/1970 Bambara
3,701,297 A 10/1972 Kovic
3,718,328 A 2/1973 Comstock
3,746,183 A 7/1973 Stemme
3,782,564 A 1/1974 Burt
3,822,008 A 7/1974 Benner, Jr.
3,841,503 A 10/1974 Hollenbach
3,871,156 A 3/1975 Koenig
3,937,458 A 2/1976 Langen
3,998,356 A 12/1976 Christensen
4,194,442 A 3/1980 Martelli
4,338,083 A 7/1982 Andrae
4,385,859 A 5/1983 Goossens
4,535,890 A 8/1985 Artusi
4,537,587 A 8/1985 Langen
4,569,435 A 2/1986 McGovney
4,655,026 A 4/1987 Wigoda
4,760,909 A 8/1988 Dudley et al.
4,822,234 A 4/1989 Johnson et al.
4,850,783 A 7/1989 Maekawa
4,870,799 A 10/1989 Bergerioux et al.
4,874,076 A 10/1989 Kaplan et al.
4,880,102 A 11/1989 Indrebo
4,901,843 A 2/1990 Lashyro
4,930,976 A 6/1990 Spacher et al.
5,054,761 A 10/1991 Dietrich et al.
5,061,231 A 10/1991 Dietrich et al.
5,102,283 A 4/1992 Balzola Elorza
5,104,369 A 4/1992 Calvert
5,161,791 A 11/1992 Akiyama et al.
5,271,703 A 12/1993 Lindqvist et al.
5,288,201 A 2/1994 Pippin
5,299,907 A 4/1994 Dal Pozzo
5,322,406 A 6/1994 Pippin et al.
5,392,927 A 2/1995 Haverkamp Begemann et al.
5,431,299 A 7/1995 Brewer et al.
5,451,086 A 9/1995 Pazzaglia
5,454,688 A 10/1995 Pippin
5,468,110 A 11/1995 McDonald et al.
5,511,772 A 4/1996 Ganz et al.
5,533,606 A 7/1996 Yuyama
5,551,822 A 9/1996 Pippin et al.
5,564,893 A 10/1996 Tacchi et al.
5,573,368 A 11/1996 Freudelsperger
5,582,324 A 12/1996 Pippin et al.
5,597,995 A 1/1997 Williams et al.
5,604,692 A 2/1997 Yuyama
5,666,492 A 9/1997 Rhodes et al.
5,672,039 A 9/1997 Perry et al.
5,713,718 A 2/1998 Okura et al.
5,720,154 A * 2/1998 Lasher ...................... G07F 5/18
53/411
5,720,157 A 2/1998 Ross
5,755,551 A 5/1998 Saeki et al.
5,755,552 A 5/1998 Iwasaka et al.
5,758,095 A 5/1998 Albaum et al.
5,768,139 A 6/1998 Pippin et al.
5,771,657 A 6/1998 Lasher et al.
5,772,392 A 6/1998 Okura et al.
5,797,515 A 8/1998 Lift et al.
5,832,693 A 11/1998 Yuyama et al.
5,833,599 A 11/1998 Schrier et al.
5,912,818 A 6/1999 McGrady
5,930,145 A 7/1999 Yuyama et al.
5,934,864 A 8/1999 Lyon et al.
5,945,651 A 8/1999 Chrosinski et al.
RE36,329 E 10/1999 Laroche
5,963,453 A 10/1999 East
5,970,462 A 10/1999 Reichert
5,988,858 A 11/1999 Yuyama et al.
5,992,742 A 11/1999 Sullivan et al.
6,061,607 A 5/2000 Bradley et al.
6,064,921 A 5/2000 Pippin et al.
6,068,156 A 5/2000 Liff et al.
6,101,787 A 8/2000 Brintazzoli et al.
6,152,364 A 11/2000 Schoonen et al.
6,170,230 B1 1/2001 Chudy et al.
6,170,634 B1 1/2001 Jaquet
6,202,923 B1 3/2001 Boyer et al.
6,206,590 B1 3/2001 Thomas et al.
6,219,587 B1 * 4/2001 Ahlin .................. G07F 17/0092
700/233
6,247,890 B1 6/2001 Chang et al.
6,256,967 B1 7/2001 Hebron et al.
6,260,761 B1 7/2001 Peoples, Jr.
6,289,260 B1 9/2001 Bradley et al.
6,308,109 B1 10/2001 Yuyama et al.
6,317,648 B1 11/2001 Sleep et al.
6,347,709 B1 2/2002 Biehl et al.
6,367,232 B2 4/2002 Kim
6,370,841 B1 4/2002 Chudy et al.
6,377,867 B1 4/2002 Bradley et al.
6,383,123 B1 5/2002 Ehring et al.
6,446,416 B1 9/2002 Kuhn et al.
6,449,927 B2 9/2002 Hebron et al.
6,474,635 B2 11/2002 Ruf et al.
6,522,945 B2 2/2003 Sleep et al.
6,564,121 B1 5/2003 Wallace et al.
6,597,969 B2 7/2003 Greenwald et al.
6,625,952 B1 9/2003 Chudy et al.
6,636,780 B1 10/2003 Haitin et al.
6,687,676 B1 2/2004 Denny
6,711,460 B1 3/2004 Reese
6,728,684 B1 4/2004 Reichert
6,742,671 B2 6/2004 Hebron et al.
6,837,664 B2 1/2005 Blakesley et al.
6,847,861 B2 1/2005 Lunak et al.
6,883,681 B1 4/2005 Coughlin et al.
6,892,512 B2 * 5/2005 Rice ...................... B65C 9/0015
53/445

(56) References Cited

U.S. PATENT DOCUMENTS

| | | | | |
|---|---|---|---|---|
| 6,892,941 | B2 * | 5/2005 | Rosenblum | G06Q 10/10 235/383 |
| 6,910,601 | B2 | 6/2005 | Thomas | |
| 6,964,146 | B2 | 11/2005 | LaRocca | |
| 6,970,769 | B2 | 11/2005 | Rice et al. | |
| 6,983,579 | B2 | 1/2006 | Rice et al. | |
| 7,006,893 | B2 * | 2/2006 | Hart | G16H 15/00 700/235 |
| 7,010,389 | B2 | 3/2006 | Lunak et al. | |
| 7,010,899 | B2 | 3/2006 | McErlean et al. | |
| 7,058,584 | B2 | 6/2006 | Kosinski et al. | |
| 7,072,737 | B2 | 7/2006 | Lunak et al. | |
| 7,100,792 | B2 | 9/2006 | Hunter et al. | |
| 7,110,855 | B2 | 9/2006 | Leishman | |
| 7,121,427 | B2 | 10/2006 | Guerra | |
| 7,123,989 | B2 | 10/2006 | Pinney et al. | |
| 7,155,306 | B2 | 12/2006 | Haitin et al. | |
| 7,185,476 | B1 | 3/2007 | Siegel | |
| 7,185,477 | B2 | 3/2007 | Rice et al. | |
| 7,249,688 | B2 * | 7/2007 | Hunter | B65G 25/02 221/87 |
| 7,325,703 | B2 | 2/2008 | Gherdan | |
| 7,988,406 | B2 | 8/2011 | Schafer | |
| 8,009,913 | B2 * | 8/2011 | Greyshock | G06V 10/24 382/181 |
| 8,695,779 | B2 * | 4/2014 | Hawkes | G16H 20/13 198/803.14 |
| 8,989,896 | B2 | 3/2015 | Brown | |
| 9,073,206 | B2 | 7/2015 | Carson | |
| 9,745,131 | B2 | 8/2017 | Hawkes | |
| 10,293,963 | B2 | 5/2019 | Hellenbrand | |
| 10,586,418 | B2 | 3/2020 | Greyshock | |
| 10,678,228 | B2 | 6/2020 | Voorhies | |
| 10,916,340 | B2 | 2/2021 | Hawkes | |
| 10,998,094 | B1 | 5/2021 | Chiu | |
| 11,126,807 | B2 | 9/2021 | Wagner | |
| 11,735,304 | B2 | 8/2023 | Chambers | |
| 11,861,554 | B2 | 1/2024 | Eller | |
| 2003/0200726 | A1 | 10/2003 | Rast | |
| 2004/0040975 | A1 | 3/2004 | Hunter et al. | |
| 2004/0069674 | A1 | 4/2004 | Siegel | |
| 2004/0088187 | A1 | 5/2004 | Chudy et al. | |
| 2004/0220694 | A1 | 11/2004 | Stingel et al. | |
| 2005/0021173 | A1 | 1/2005 | Pinney et al. | |
| 2007/0145066 | A1 | 6/2007 | Knoth | |
| 2007/0162179 | A1 | 7/2007 | Freudelsperger | |
| 2007/0270998 | A1 | 11/2007 | Luciano et al. | |
| 2008/0006647 | A1 | 1/2008 | Hunter et al. | |
| 2008/0138187 | A1 | 6/2008 | Christ | |
| 2010/0089936 | A1 | 4/2010 | Luciano | |
| 2010/0176145 | A1 | 7/2010 | Hawkes et al. | |
| 2015/0058041 | A1 | 2/2015 | Ervin | |

OTHER PUBLICATIONS

Mexican Office Action issued Sep. 2, 2014 in Patent Application No. 2011/005873 (with English Translation).

Mexican Communication of Substantive Examination, dated Mar. 27, 2014, Folio No. 27167 issued in PCT Patent Application No. MX/a/2011/005873 filed On Dec. 4, 2009, (4) pages.

Office Action issued Mar. 17, 2016, in Korea Patent Application No. 2011-7015449, 2 pgs.

Extended European Search Report issued May 6, 2016 in Patent Application No. 09831183.0.

Office Action issued on Jul. 5, 2016 in Canadian Patent Application No. 2,745,147.

Office Action issued on Aug. 16, 2016 in Mexican Patent Application No. MX/a/2014/014638, filed Jun. 3, 2011.

Office Action issued Sep. 29, 2016, in Korean Patent Application No. 2014-7015449 (English Translation provided).

Office Action issued May 23, 2017, in Canada Patent Application No. 2,745,147.

Office Action issued Jul. 21, 2016, in Mexican Patent Appln. MX/a/2014/014638 (English Translation provided).

Mexican Communication of substantive Examination, dated Sep. 2, 2014, Folio 73756 issued in PCT Patent Appln No. MX/a/2011/005873 filed on Dec. 4, 2009, (4 Pages).

Australian Government Patent Examination Report No. 1, dated Mar. 17, 2015 in Au Patent Appln . No.2009322199.

Combined Chinese Office Action and Search Report issued Nov. 5, 2012 in Chinese Patent Appln. No. 200980155637.5 (with English Translation of Categories of Cited Documents).

International Searching Authority, the International Search Report and the Written Opinion of the International Searching Authority, of the Declaration, PCT US2009/066758, Feb. 1, 2010, 22 pages.

Communication pursuant to Article 94(3) EPC issued Jul. 26, 2018 in European Patent Application No. 09 831 183.0.

Office Action issued May 13, 2019 in corresponding Canadian Patent Application No. 2,989,635, 4 pages.

* cited by examiner

APPARATUS AND METHODS FOR AUTOMATED PICKING OF ITEMS

This Application is a Continuation of U.S. application Ser. No. 18/189,771, filed Mar. 24, 2023, allowed, which is a Continuation of U.S. application Ser. No. 16/984,986, filed Aug. 4, 2020, patented, which is a Continuation of U.S. application Ser. No. 15/893,066 filed Feb. 9, 2018, patented, which is a Continuation of U.S. application Ser. No. 14/859,778, filed Sep. 21, 2015, patented, which is a continuation of U.S. application Ser. No. 12/559,601 filed Sep. 15, 2009, patented, and claims priority to U.S. Provisional Patent Application Ser. No. 61/120,209, filed Dec. 5, 2008, and the entire content of each is hereby incorporated by reference in their entirety.

TECHNICAL FIELD

The present invention relates generally to a device for the picking of stored items, and more particularly to a system for automatically picking medications, supplements, or other items to fill orders.

BACKGROUND

Hospitals, long term care and other health care facilities distribute and administer pharmaceutical products to patients in individual doses numerous times per day. Pharmaceutical products such as prescription medications, nutritional supplements and the like are often stored in bulk by pharmacies and are repackaged into containers of multiple doses based on individual prescriptions for retail or outpatient distribution. For inpatient or in-facility distribution, pharmacies also often repackage bulk pharmaceuticals into "unit of use" or "unit dose" packages, for example, multiple blister packs that are connected together in a strip that contain multiple single doses of the pharmaceutical product.

The traditional method for distributing individual dosage units of pharmaceutical products to patients begins with the generation of a patient order by a physician for particular medications. The patient order is delivered to the pharmacy. There, the process of interpreting the patient order, pulling the specified medication or supplements from the drug storage areas, packaging the medication or supplements, and labeling the package is routinely done manually by pharmacy support personnel. After a final check by the facility pharmacist, the packaged individual dosage units are ready for distribution. In large facilities, the packages containing the patient's order are forwarded to individual nursing units where nursing staffers distribute and administer them to the patients.

There are several disadvantages associated with the traditional method of distributing individual dosage units of pharmaceutical products. To begin with, the process is labor and cost intensive. Many separate labor steps are required to fill a single patient order. In large facilities servicing hundreds of patients each day, the staffing requirements to rapidly process patient orders are substantial. In addition, with so many human inputs required in the existing process, there may also be a risk of human error.

As an attempt to address at least some of the issues with respect to staffing requirements and human error, a variety of automated medication dispensing systems have been developed. The current landscape for automated medication dispensing is dominated by a 30-day system utilizing either "bingo cards" or unit doses supplied in a 30-day box. The known systems provide a 30-day or other multi-day supply for each patient pass-time for each prescription on a relatively long term basis. In the event the patient is discharged or the treatment is changed, the unused portion of the 30-day supply cannot be cost effectively reused even though the product may be labeled appropriately. The labor cost required to reintroduce the pharmaceutical products into the distribution system and to maintain the integrity and traceability of manufacturer and expiration data exceeds the value of the pharmaceutical products, even if the substantial restocking fees are paid by the healthcare system. As a result, such unused pharmaceutical products are returned to the pharmacy for disposal. This disposal of unused pharmaceutical products is a significant waste of those resources as well as a detriment to the environment.

One known pharmaceutical package dispensing system automates various aspects of the task of filling patient orders for units of use pharmaceuticals. The system employs a number of storage cartridges arranged in stacked rows on a frame. The cartridges contain strips of unit dose packages of pharmaceutical products. The packages consist of individual unit dose blisters. Each of the blisters contains a unit of use, e.g., a single tablet or capsule. Several blister packages are joined together to form the linear strips such that a given cartridge may contain several such strips stacked vertically or in roll form. Each cartridge is provided with a forward-facing opening through which a portion of the lowermost blister strip contained therein projects. A pick head is movable adjacent a respective row of cartridges to a desired location adjacent a cartridge. The pick head pulls the blister strip out of the cartridge and a cutting blade mounted on the pick head cuts an individual blister from the strip. The severed blister pack free-falls onto a conveyor or into a bin on the pick head or elsewhere and when the pick head has finished picking blisters for the order, it discharges the blisters in the bin onto a tray. The tray serves as an accumulation point servicing multiple pick heads. The tray is moved to a discharge location to dump the blisters by gravity from the tray into a funnel of a packaging station.

The drug dispensing machine described above and similar such systems have several disadvantages. To begin with, only one tray and discharge slide for the multiple pick heads is provided. Therefore, a pick head may have to wait for a tray to empty, which significantly reduces the picking efficiency of the pick heads and throughput of the dispensing machine. Second, the cartridge, pick head and bin design can lead to difficulties when a given blister strip is pulled, cut and dropped from the cartridge. The opening through which the blister strips project allows for significant lateral play by the strips. Further, the size of the unit doses may vary greatly and pick head retrieval and cutting mechanisms must be adjusted to accommodate unit doses of different sizes. This can lead to misalignments with the cutting blade. The gravity free-fall of the severed unit doses often results in missing or jammed unit doses producing incomplete orders and requiring manual intervention to dislodge, retrieve and/or collect the errant unit doses.

There is a continuing need to improve a system and overall methodology for dispensing medication orders for individual patients in health care facilities.

SUMMARY

The present invention overcomes the foregoing and other shortcomings and drawbacks of dispensing systems heretofore known for use in filling orders for medications and/or supplements. While the invention will be described in connection with certain embodiments, it will be understood that the invention is not limited to these embodiments. On the contrary, the invention includes all alternatives, modifications and equivalents as may be included within the spirit and scope of the present invention.

According to one aspect of the present invention, a system for assembling and dispensing an order made up of one or more individually packaged items from a plurality of different individually packaged items includes a storage module containing one or more packages of each of the items, and a conveyor having selectively assignable spaces configured to receive the packaged items associated with a particular order and to transport the packaged items to a processing location. The system further includes a pick device that is movable relative to the storage module and configured to retrieve a package from the storage module. A transfer station adjacent the conveyor receives one or more of the packaged items from the pick device and an actuator associated with the transfer station moves the packaged items from the transfer station to the conveyor when the assigned space associated with the order is in registration with the transfer station.

In another aspect, the system further includes a transfer nest that is movable with the pick device and which receives the packaged items from the pick device and transfers the packaged items to the transfer station. The transfer nest and/or the transfer station may have slots or channels that are shaped complimentary to the shape of the packages containing the items such that the packages are constrained for movement only along longitudinal directions of the slots or channels. Movement of the packages between the storage module and the processing location is positively controlled and the packages are not permitted to move in an unconstrained manner.

In another aspect, a method of filling an order that includes one or more individually packaged items selected from a plurality of different individually packaged items includes assigning a dedicated space on a conveyor for receiving one or more of the packaged items, moving the conveyor toward a processing location, picking a packaged item from a storage location, moving the item to a transfer station, and moving the item from the transfer station to the dedicated space on the conveyor when the dedicated space is in registration with the transfer station.

The above and other objects and advantages of the present invention shall be made apparent from the accompanying drawings and the description thereof.

DETAILED DESCRIPTION

Figure 1:
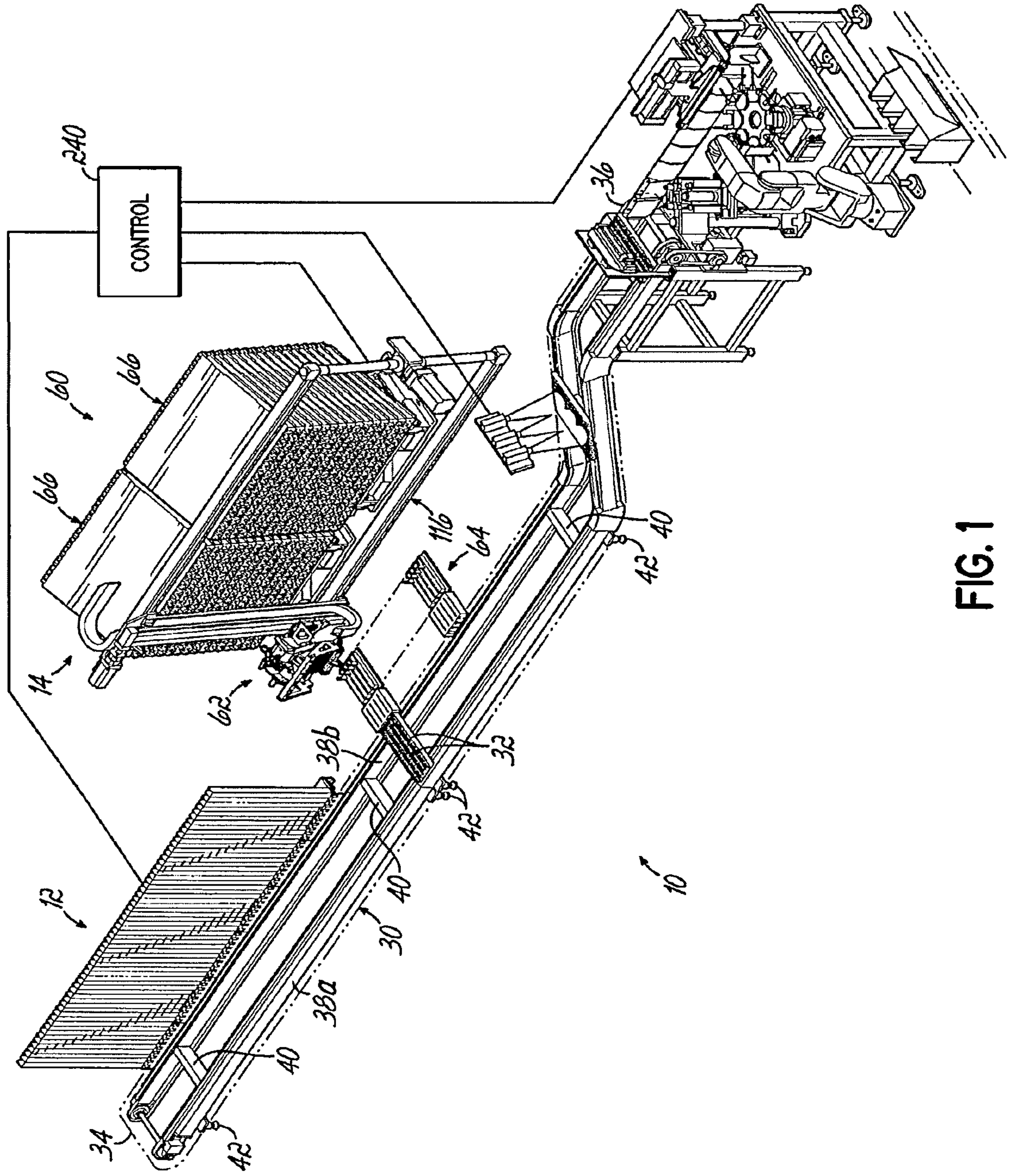
FIG. 1 is a perspective view of an exemplary system for storing and dispensing medications and supplements in accordance with the present disclosure.

FIG. 1 depicts an exemplary automated dispensing system 10 in accordance with the principles of the present disclosure. In the embodiment shown, the dispensing system 10 is configured to store and dispense individually packaged and labeled doses of medications/supplements, and to assemble the dispensed medications/supplements into individual medication orders, such as time-pass medication orders to be delivered to a long-term care facility, for example. It will be appreciated, however, that a dispensing system in accordance with the present disclosure may alternatively be configured to dispense other items. The dispensing system 10 is divided into distinct modules that are dedicated to dispensing the medications/supplements based on the demand, or order frequency, of those items. In the embodiment shown, a first module 12 is configured to dispense medications/supplements having a relatively high demand or order frequency, and a second module 14 of the dispensing system 10 is configured to store and dispense medications/supplements having a relatively lower demand or order frequency.

Figure 2:
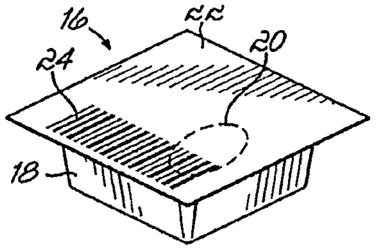
FIG. 2 is a perspective view of an exemplary package for containing a single dose of a medication/supplement in accordance with the present disclosure.

In the embodiment shown and described herein, the medications/supplements are provided in packages 16 sized to receive an individual dose of a particular medication/supplement, commonly referred to as a blister pack. With reference to FIG. 2, an exemplary package 16 comprises a base portion 18 defining a cavity for receiving the individual dose of the medication/supplement 20, and a generally planar closure 22 disposed over an open end of the base portion 18. The packages 16 may be provided with information 24 related to the medication/supplement 20 contained in the packages 16, such as the name of the medication/supplement 20, the manufacturer, the date manufactured, the lot number, and/or other information. In the embodiment shown, information 24 is provided on the closure 22 and includes machine-readable information, such as a bar-code, that may be used to facilitate the automated storing, tracking, dispensing, and packaging of orders.

With continued reference to FIG. 1, the dispensing system 10 further includes an endless conveyor 30 comprising a plurality of carriers 32 that move past the first, high-demand module 12 and the second, low-demand module 14 to collect ordered medications/supplements and carry them to a designated location for further processing. In the embodiment shown, a first end 34 of the conveyor 30 is positioned adjacent the high-demand module 12. The carriers 32 are moved along the conveyor 30 past the high-demand module 12 and the low-demand module 14 toward a second end 36 where the medications/supplements are packaged for delivery to a long term care facility. In the embodiment shown in FIG. 1, the conveyor 30 comprises a pair of oppositely disposed, longitudinally extending rails 38*a*, 38*b* supporting the plurality of carriers 32. The conveyor 30 may further comprise cross-members 40 extending between the rails 38*a*, 38*b* and support legs 42 configured to support the longitudinally extending rails 38*a*, 38*b* a distance above a floor surface.

Figure 3:
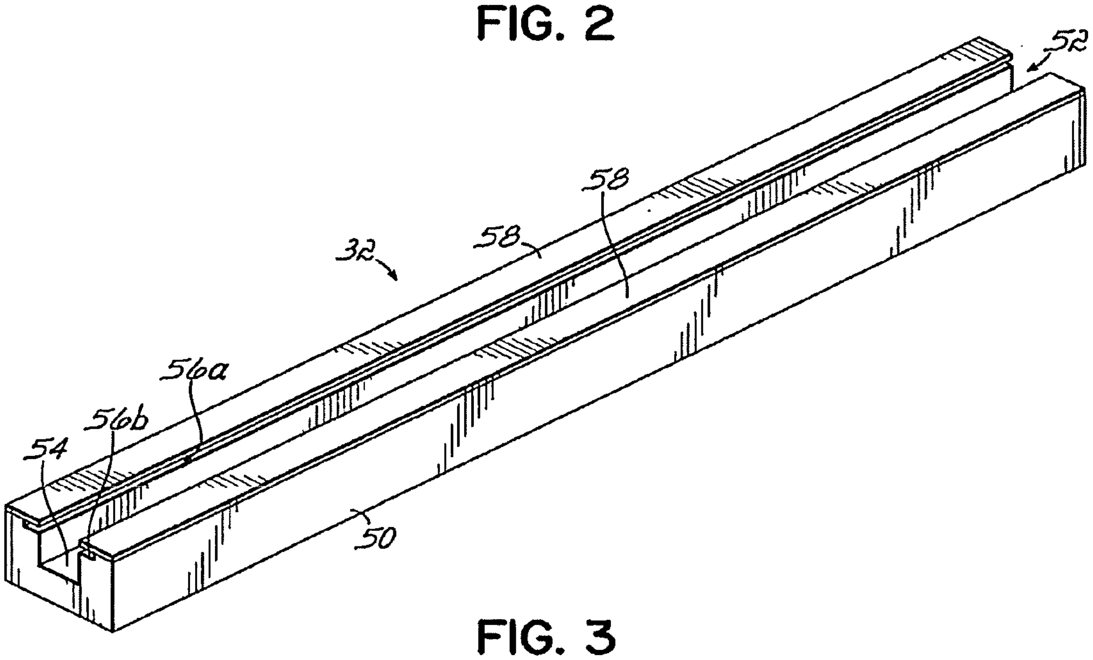
FIG. 3 is a perspective view of an exemplary carrier of a conveyor in accordance with the present disclosure.
Figure 3A:
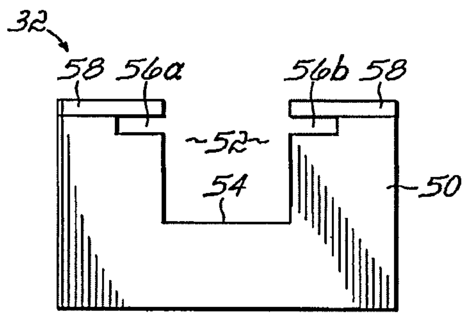
FIG. 3A is an end elevation view of the carrier of FIG. 3.

FIGS. 3 and 3A depict an exemplary carrier 32 comprising an elongate, generally rectangular body 50 having a longitudinal channel 52 formed into one side and extending between the ends of the body 50. The channel 52 is shaped complementarily to the shape of the packages 16 and includes a deep central portion 54 and shallower side portions 56*a*, 56*b* disposed on opposite sides of the central portion 54, whereby a package 16 can be received in the channel 52 with the base 18 positioned in the central portion 54 and the sides of the closure 22 supported on the side portions 56*a*, 56*b*. The side portions 56*a*, 56*b* are enclosed at their upper ends, such as by top plates 58 or other structure so that packages 16 received in the channel 52 are constrained for movement only along a longitudinal direction of the channel 52. The focus of this disclosure is the low-demand module 14 of the dispensing system, depicted in more detail in FIG. 4 and discussed below.

Figure 4:
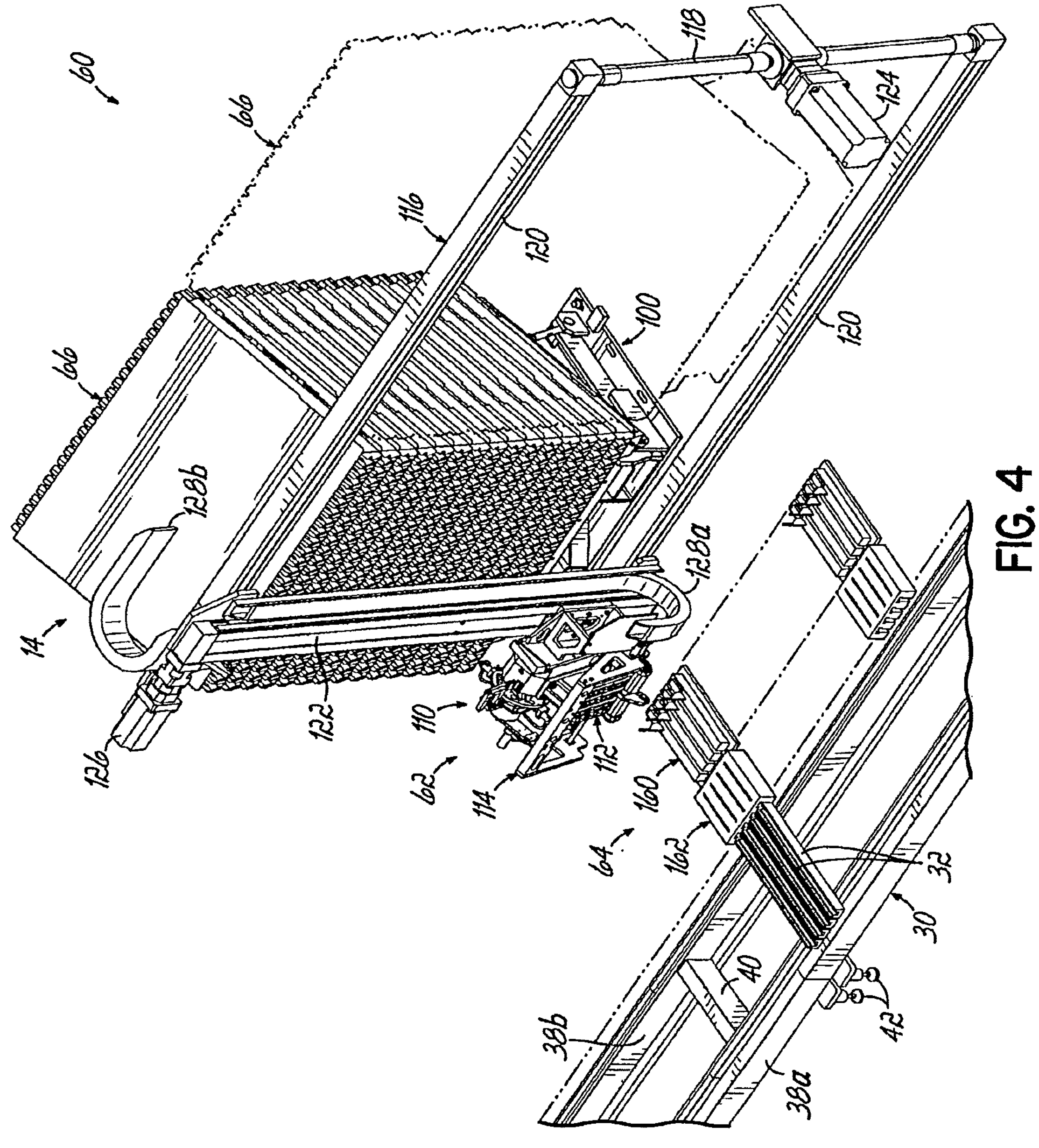
FIG. 4 is an enlarged perspective view of the storage module, conveyor, gantry, and pick device of FIG. 1.

Referring now to FIG. 4, the low-demand module 14 comprises a storage module 60 for storing the individually packaged and labeled medications/supplements, a pick device 62 for retrieving selected medications/supplements from the storage module 60, and a transfer station 64 for delivering the selected medications/supplements to the carriers 32 of the conveyor 30 to fill orders. The storage module 60 comprises one or more storage units 66 positioned alongside the conveyor 30, as may be desired, to accommodate storage of the medications/supplements needed to fill the medical orders. With continued reference to FIG. 4, and referring further to FIGS. 5-7, each storage unit 66 comprises a plurality of generally rectangular, vertically-spaced plates 68 and a plurality of laterally spaced walls 70 disposed between each plate 68 to define an array of elongate bins 72 configured to receive storage tubes 74 containing stacked packages 16 of the individually packaged medications/supplements. The storage tubes 74 are slidably received in the respective bins 72 at first, receiving ends 76 of the bins 74.

Figure 7:
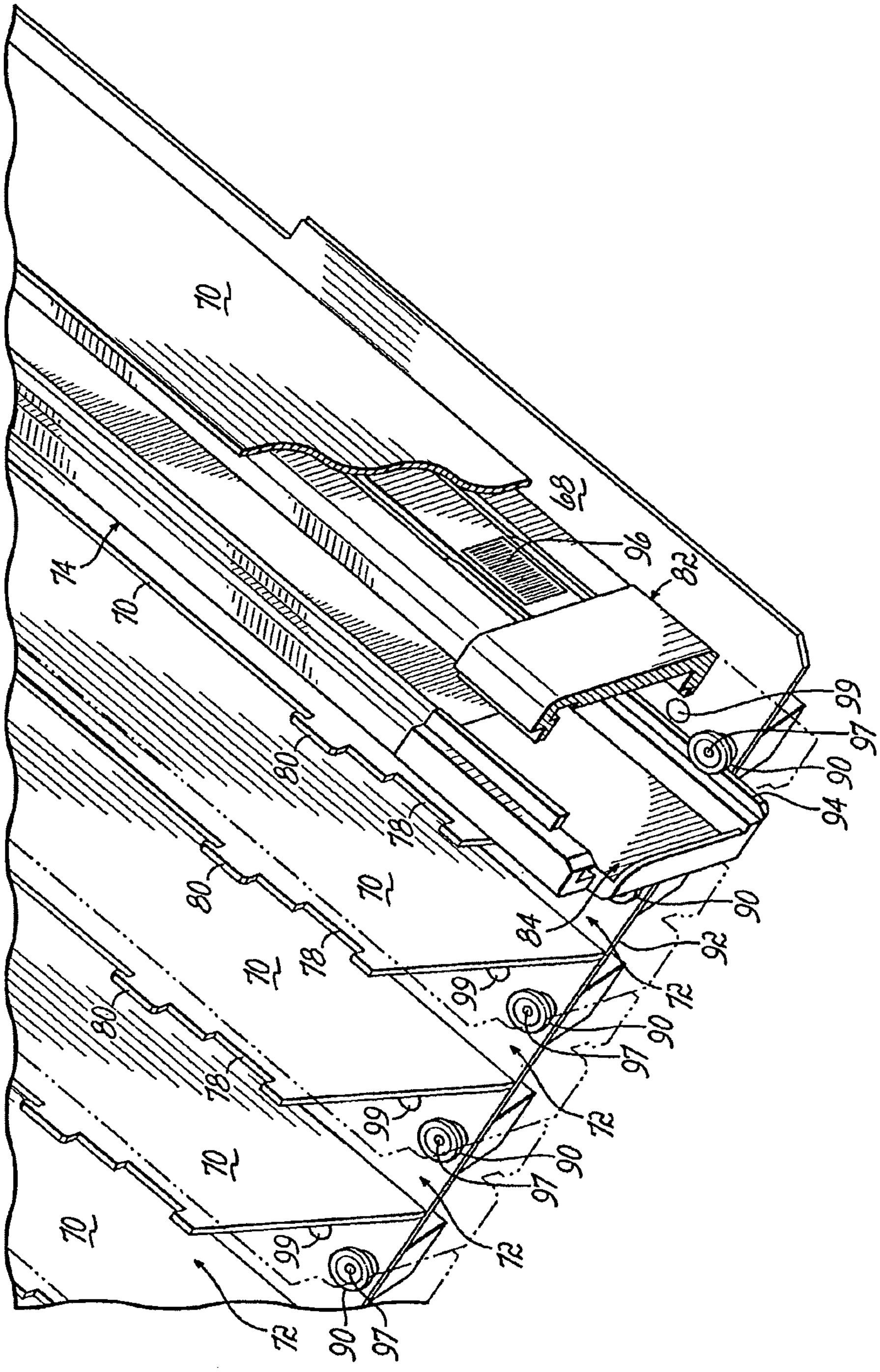
FIG. 7 is an enlarged perspective view of the storage module depicted in FIG. 6.

In the embodiment shown, the plates 68 and walls 70 of the storage unit 66 are formed from aluminum sheet material. The walls 70 are formed with notches 78 and tabs 80, and the plates 68 are formed with corresponding slots (not shown) whereby the walls 70 and plates 68 may be assembled together to form the array of bins 72. In the embodiment shown, the bins 72 have a generally rectangular cross-sectional shape, as do the storage tubes 74 that are received within the respective bins 72. In this embodiment, the tubes 74 are formed from extruded plastic material and an end cap 82 disposed at one end of the tube 74 facilitates dispensing the packages 16 therefrom. As shown in FIG. 7, the end cap 82 includes a slot 84 along an upwardly facing side of the storage tube 74 whereby an individual package 16 may be moved in a direction transverse to the longitudinal axis of the storage tube 74 for removal of the package 16 from the storage tube 74 through the slot 84. With continued reference to FIG. 7, each bin 72 is provided with a registration pin 90 proximate a second, dispensing end 92 that faces the pick device 62. As the storage tubes 74 are placed within the respective bins 72, the registration pins 90 engage another slot 94 formed on the end cap 82 to position the end cap 82 at a location that facilitates engagement and retrieval of the individual packages 16 stored in the tube 74 by the pick device 62, as will be described in more detail below.

Figure 5:
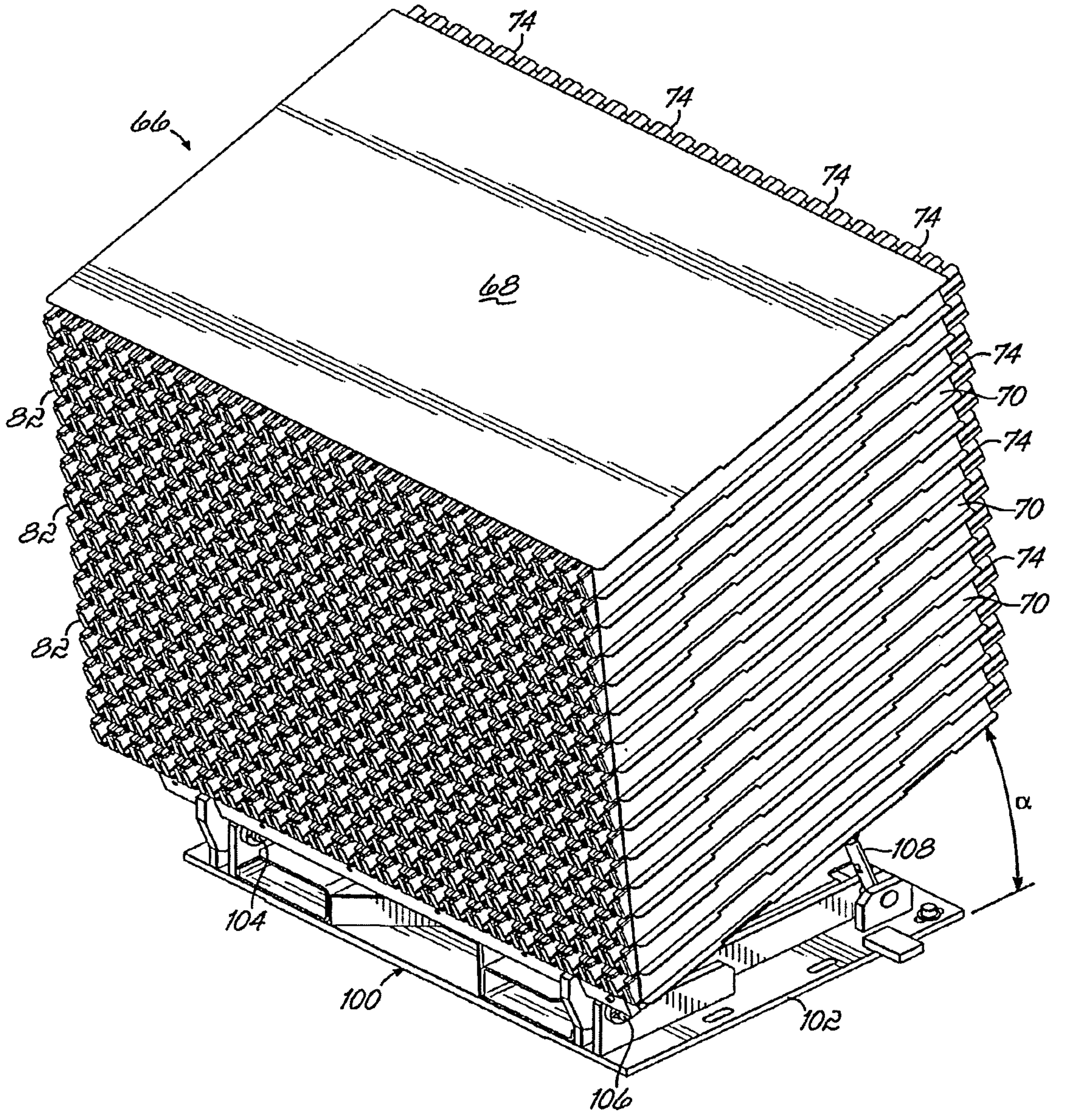
FIG. 5 is an enlarged perspective view of a portion of the storage module of FIG. 4.
Figure 6:
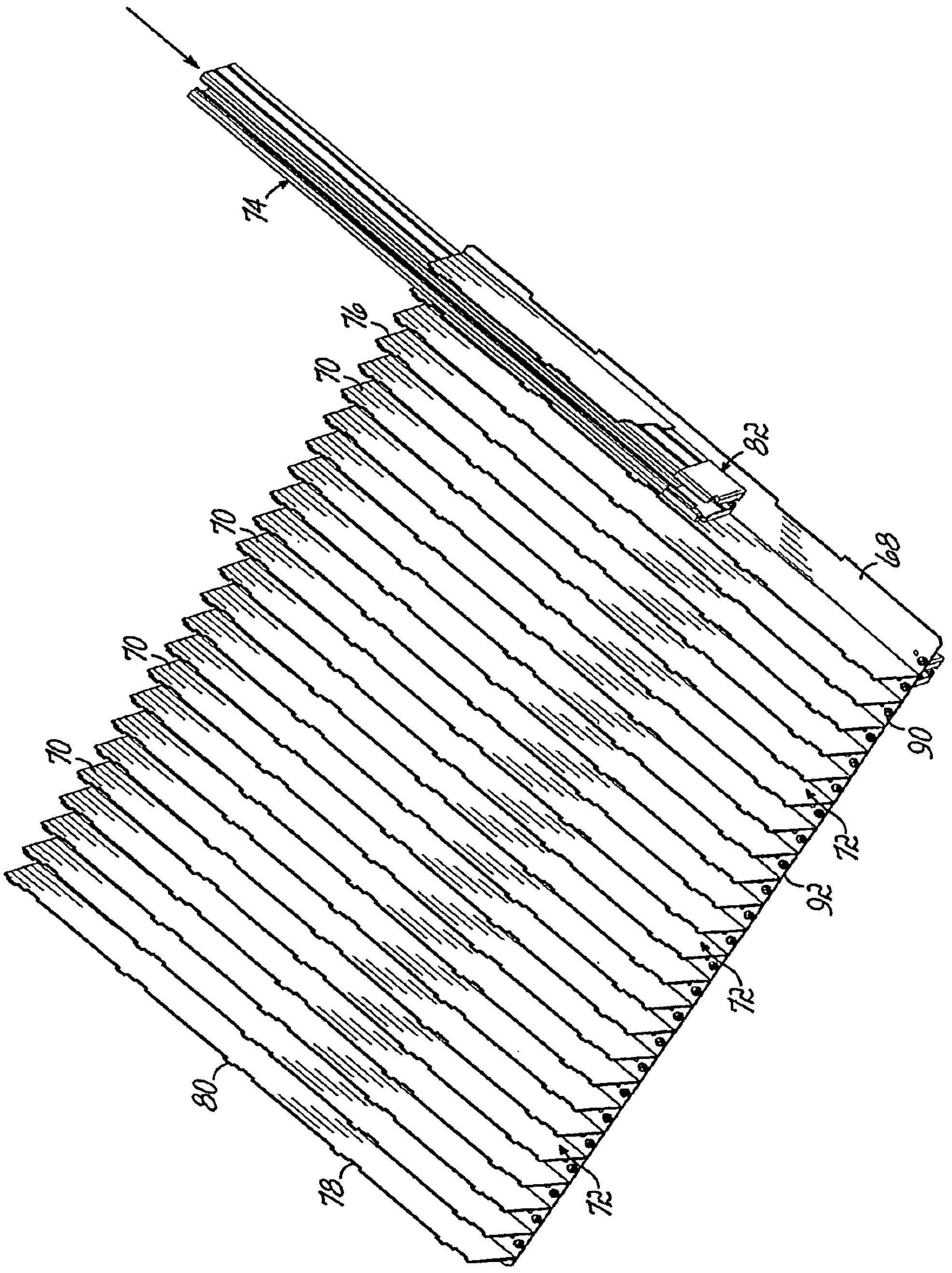
FIG. 6 is a partial exploded view of the storage module of FIG. 5.

As depicted in FIG. 5, each storage unit 66 is supported on a base 100 so that storage tubes 74 supported in the bins 72 of the storage unit 66 may be positioned for proper access by the pick device 62. The base 100 comprises a generally flat plate 102 that may be bolted or otherwise secured to the floor surface. The array of bins 72 may be pivotally coupled to the plate 102 by appropriate pin connections 104, 106, and may be adjusted to have a desired inclination angle relative to the floor surface by an adjustable link 108 coupled between the array of bins 72 and the plate 102. The inclined orientation of the bins 72 of the storage unit 66 places the dispensing ends 92 of the bins 72 at a lower elevation than the receiving ends 76.

The packages 16 of medications/supplements are stacked one atop another within the storage tubes 74, and the storage tubes 74 are slidably received within the respective bins 72 of the storage unit 66. The storage tubes 74 are inserted with the end caps 82 positioned at the dispensing ends 92 of the bins 72 such that the stacked packages 16 within the tubes 74 are urged by gravity in a direction toward the end caps 82 at the dispensing ends 92 of the bins 72. A weight (not shown) may be provided on top of the uppermost package 16 within each storage tube 74 to facilitate movement of the packages 16 toward the end caps 82. As depicted in FIG. 10B, each bin 72 may be provided with a sensor 97 proximate the dispensing end 92 for detecting the presence of packages 16 within the storage tube 74 supported in the bin 72, and for communicating with a control 240 to indicate when the storage tube 74 needs to be replaced with a storage tube 74 filled with packages 16. The bins 72 may also be provided with one or more sensors 99 for detecting the presence of a storage tube 74 in the bin, and for communicating with the control 240 when a storage tube 74 is not in the bin 72. In the embodiment shown, in FIGS. 10B and 12B, sensors 97 for detecting the pressure of packages 16 in a storage tube 74 are located with the registration pin 90.

Each storage tube 74 contains only a single type of medication/supplement, and the storage tubes 74 may be provided with information 96 identifying the particular type of medication/supplement contained within the packages 16 stacked within the tube 74 (FIG. 7). In one embodiment, the information provided on the storage tubes 74 includes machine readable information, such as bar codes, RFID, or other types of machine readable information, to facilitate the automated storage, tracking and dispensing of the medications/supplements.

Figure 8:
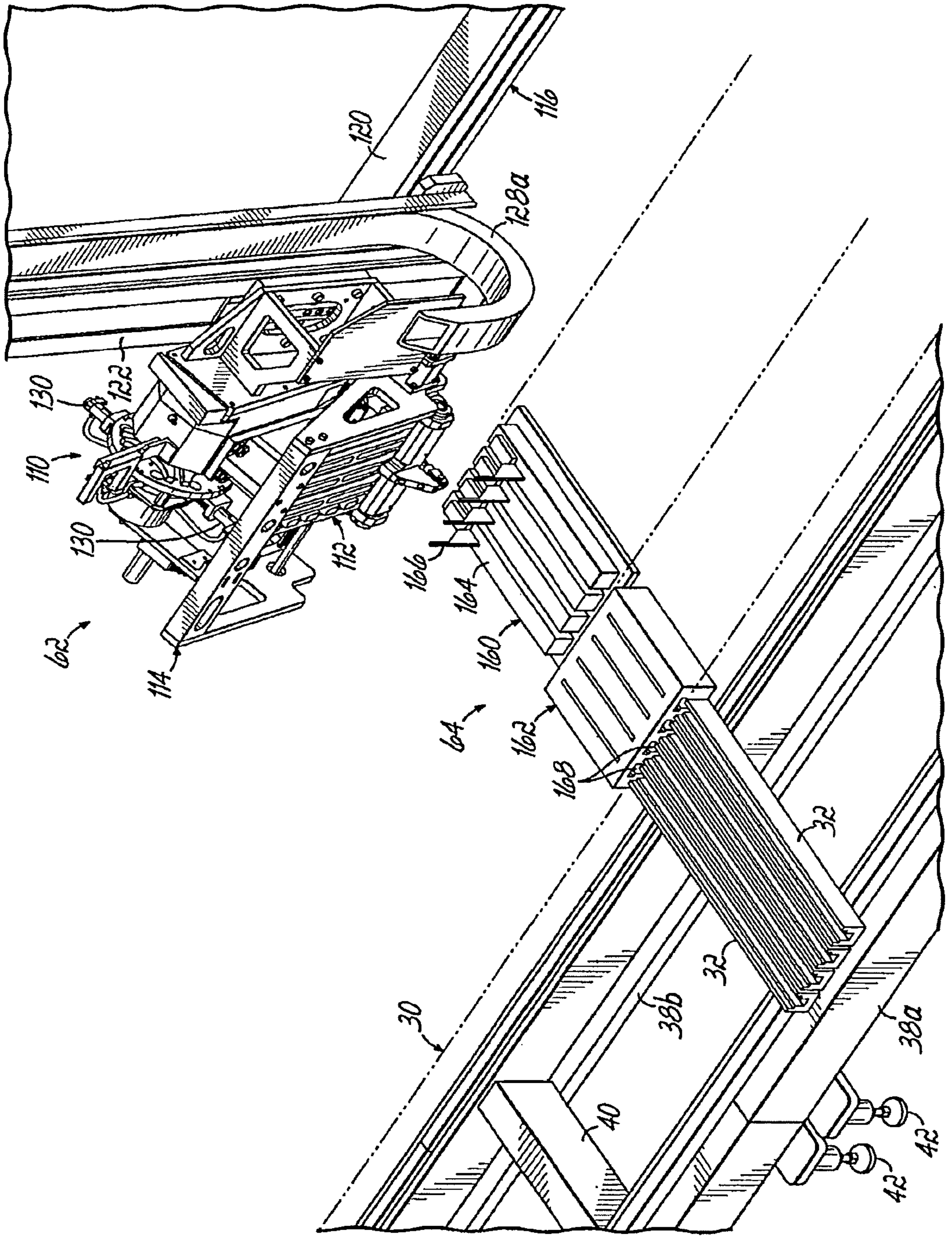
FIG. 8 is a perspective view depicting the pick device and transfer station of the low-demand module of the dispensing system.

The medications/supplements stored in the array of bins 72 of the storage units 66 of the storage module 60 are retrieved by the pick device 62 and are delivered to a transfer station 64 for subsequent transfer to a designated carrier 32 as the carrier 32 moves past the transfer station 64 on the conveyor 30, as will be described in more detail below. With reference to FIGS. 4 and 8, the pick device 62 comprises a pick head 110 and a transfer nest 112 supported on a transfer frame 114 that moves with the pick head 110. The pick device 62 is supported on a vertically inclined gantry 116 having vertical frame members 118 and horizontal frame members 120 positioned proximate the dispensing ends 92 of the bins 72 of the storage module 60 for access to the storage tubes 74. A gantry crossmember 122 is driven by a first motor 124 for movement longitudinally along the horizontal frame members 120, and a second drive motor 126 moves the pick device 62 vertically along the gantry crossmember 122 so that the pick head 110 can access any of the plurality of storage tubes 74 housed in the storage module 60. Flexible cable guides 128*a*, 128*b* may be provided adjacent the gantry crossmember 122 and/or the horizontal frame members 120 to house cables or wires extending between the pick device 62 and corresponding power supplies and/or control modules.

Figure 9:
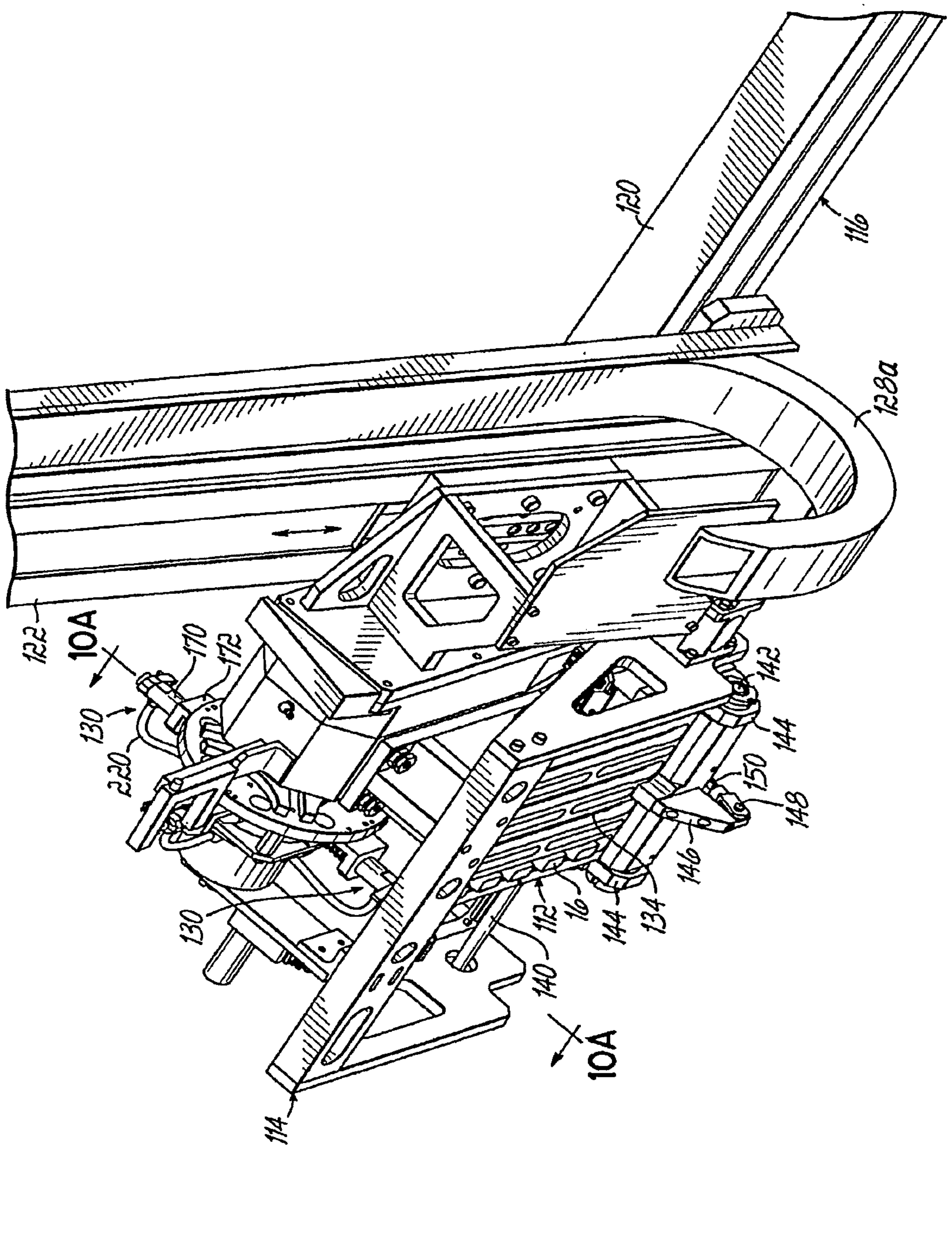
FIG. 9 is an enlarged perspective view of the pick device of FIG. 8.
Figure 9A:
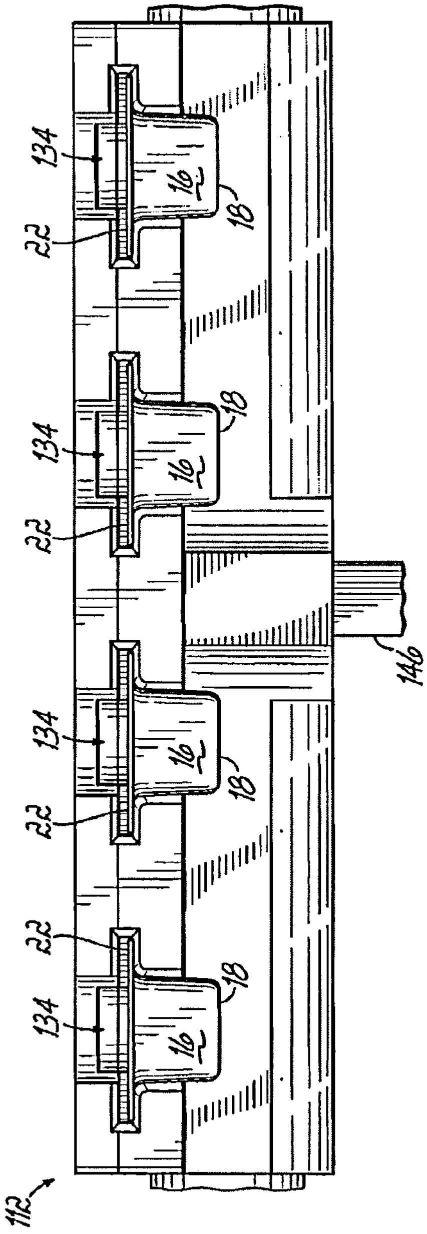
FIG. 9A is a partial detail view along line 9A-9A of FIG. 16.
Figure 10A:
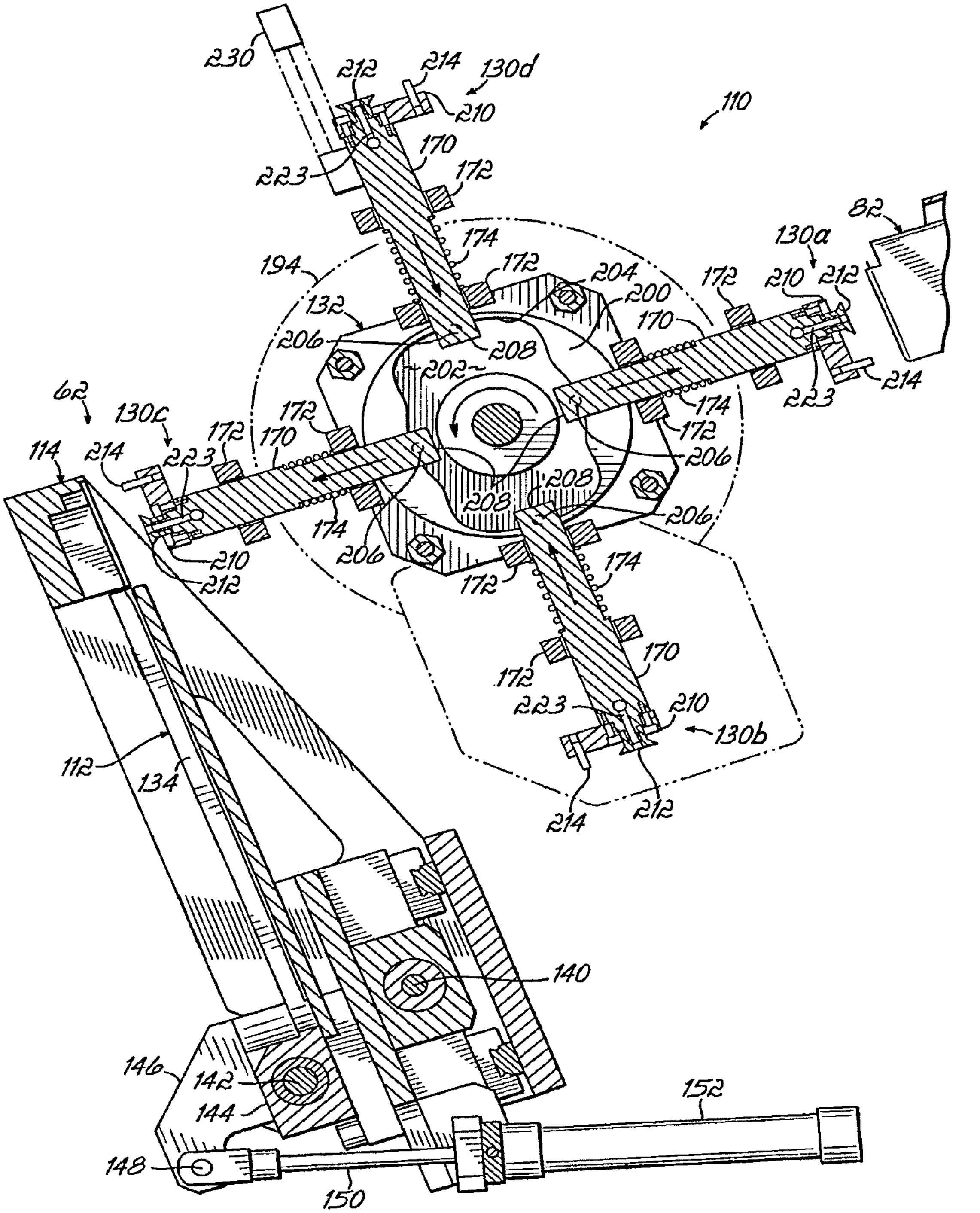
FIG. 10A is a partial cross-sectional view depicting the pick device and transfer nest taken generally along line 10A-10A of FIG. 9.
Figure 10B:
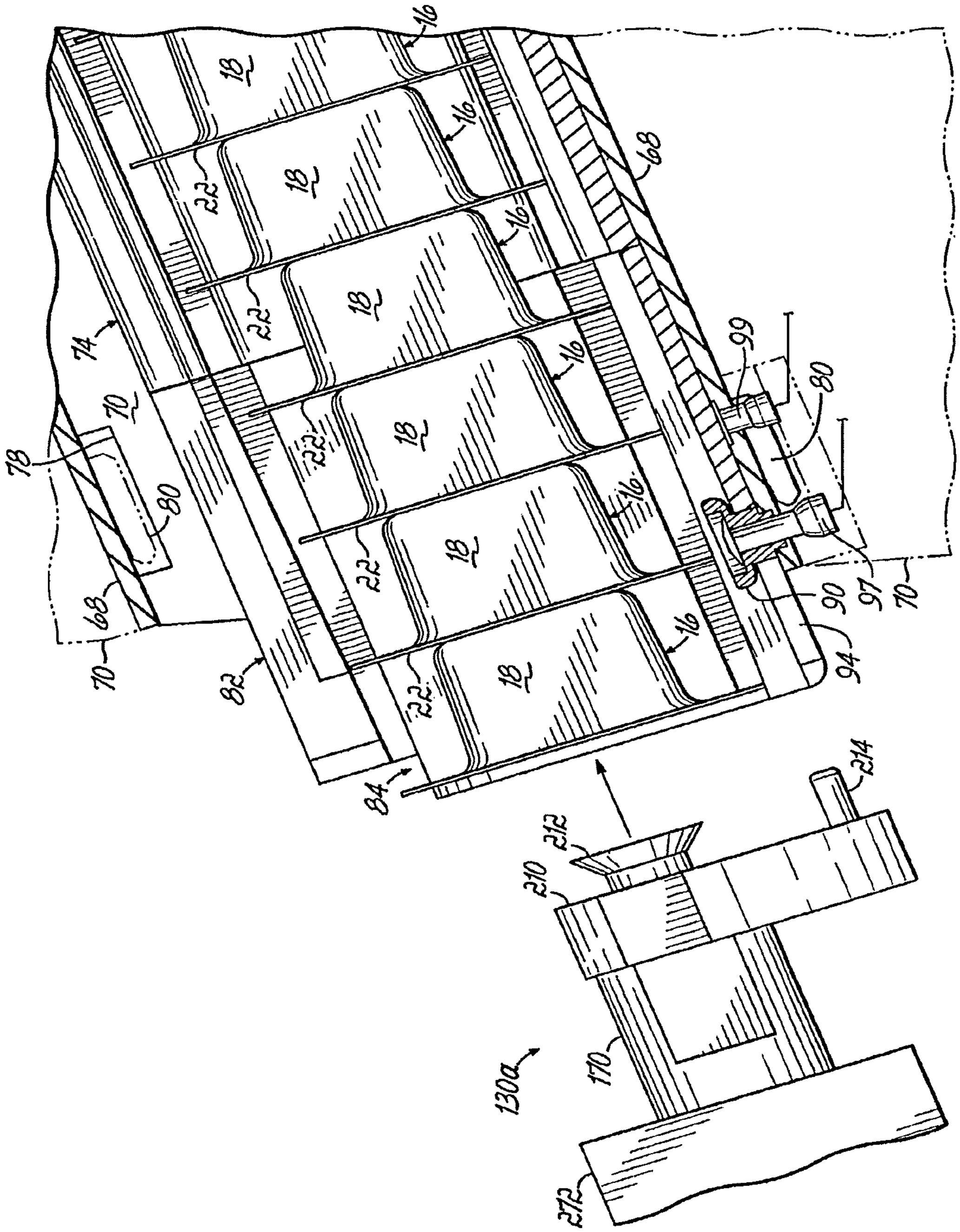
FIG. 10B is an enlarged cross-sectional detail view of FIG. 10A, illustrating a gripper and a storage tube.

As shown in FIGS. 9 and 10A, the pick head 110 comprises a plurality of grippers 130 extending from a rotatable housing 132 for engaging and retrieving selected packages 16 from the storage tubes 74 supported in the storage module 60. Four grippers 130*a*, 130*b*, 130*c*, 130*d* are depicted and are collectively referred to as "grippers 130" herein. The transfer nest 112 is supported within a transfer frame 114 coupled to the pick head 110 for movement therewith, such that packages 16 selected by the pick head 110 may be received onto the transfer nest 112 and subsequently delivered to the transfer station 64. In the embodiment shown, the transfer nest 112 includes four slots 134 for receiving the packages 16 of medications/supplements from the grippers 130 of the pick head 110. It will be appreciated, however, that the transfer nest 112 may alternatively have a fewer number or a greater number of slots 134, as may be desired. The slots 134 of the transfer nest 112 are configured to receive the packages 16 from the grippers 130 of the pick head 110 and to maintain positive control over the motion of the packages 16 as they are moved to the transfer station 64. To this end, the slots 134 are shaped complementarily to the shape of the packages 16, in a manner similar to the channels 52 of carriers 32 and as depicted in FIG. 9A.

The transfer nest 112 is movable along a shaft 140 in a longitudinal direction relative to the pick head 110 so that the selected packages 16 of medications/supplements may be received in one of the plurality of slots 134 on the transfer nest 112 by aligning a selected slot 134 in registration to receive a package 16 from the grippers 130 of the pick head 110. The transfer nest 112 is also pivotable about a shaft 142 coupled to the transfer frame 114 to position the transfer nest 112 adjacent the transfer station 64 for delivery of the selected packages 16 of medications/supplements to the transfer station 64. In the embodiment shown, the transfer nest 112 is pivotally coupled to the transfer frame 114 by a shaft 142 received in shaft supports 144 extending from the transfer frame 114. A bracket 146 extending from the transfer nest 112 is coupled at a pivot joint 148 to the end of a drive rod 150 of a pneumatic piston 152, whereby the transfer nest 112 can be pivoted around the shaft 142 by actuation of the pneumatic piston 152, from a first position wherein the transfer nest 112 is located adjacent the pick head 110 for receiving the selected packages 16 of medications/supplements (depicted in FIGS. 8 and 9), to a second position wherein the transfer nest 112 is positioned adjacent the transfer station 64 (depicted in FIG. 16).

Referring again to FIG. 8, the transfer station 64 comprises a slide assembly 160 for moving the packages 16 of medications/supplements from the transfer nest 112, and a queue support 162 for receiving the packages 16 of medications/supplements from the transfer nest 112 and supporting them until the carrier 32 assigned to receive the packages 16 of medications/supplements for a particular order is positioned at the queue support 162 in registration for receiving the packages 16. The slide assembly 160 comprises a plurality of individually actuatable slide members 164 having upwardly extendable prongs 166 that engage the packages 16 of medications/supplements supported on the transfer nest 112 when the transfer nest 112 has pivoted to the second position. The prongs 166 slide the packages 16 of medications/supplements from the transfer nest 112 into corresponding channels 168 formed in the queue support 162 of the transfer station 64. In the embodiment shown, the channels 168 formed in the queue support 162 are shaped complementarily to the shape of the packages 16 of medications/supplements, in a manner similar to the channels 52 of carriers 32, such that the packages 16 received in the respective channels 168 of the queue support 162 are constrained and allow for movement only along longitudinal directions of the channels 168.

Figure 12A:
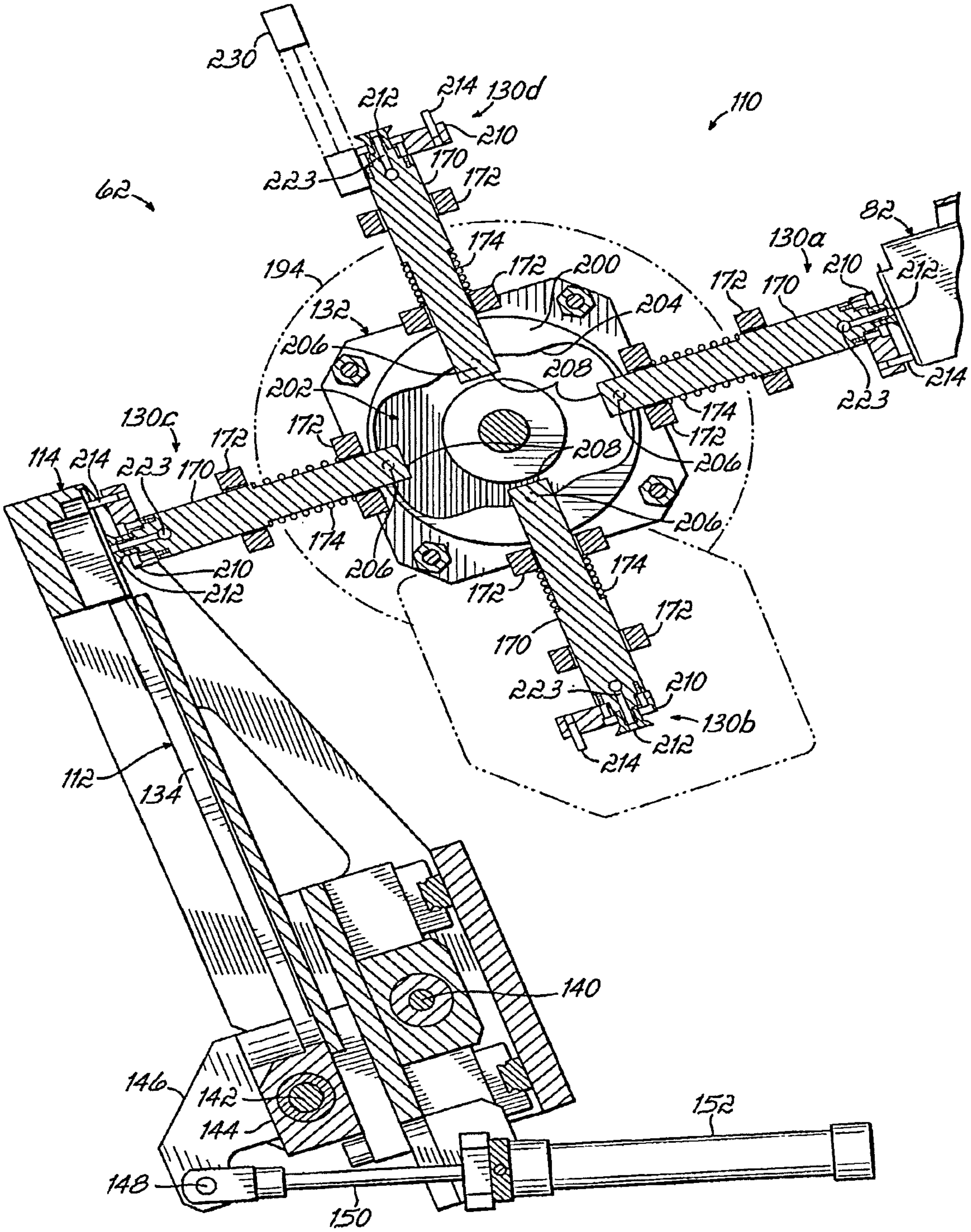
FIG. 12A is a partial cross-sectional view, similar to FIG. 10A, and depicting the rotating cam in a second position wherein a gripper is extended to engage a package.
Figure 12B:
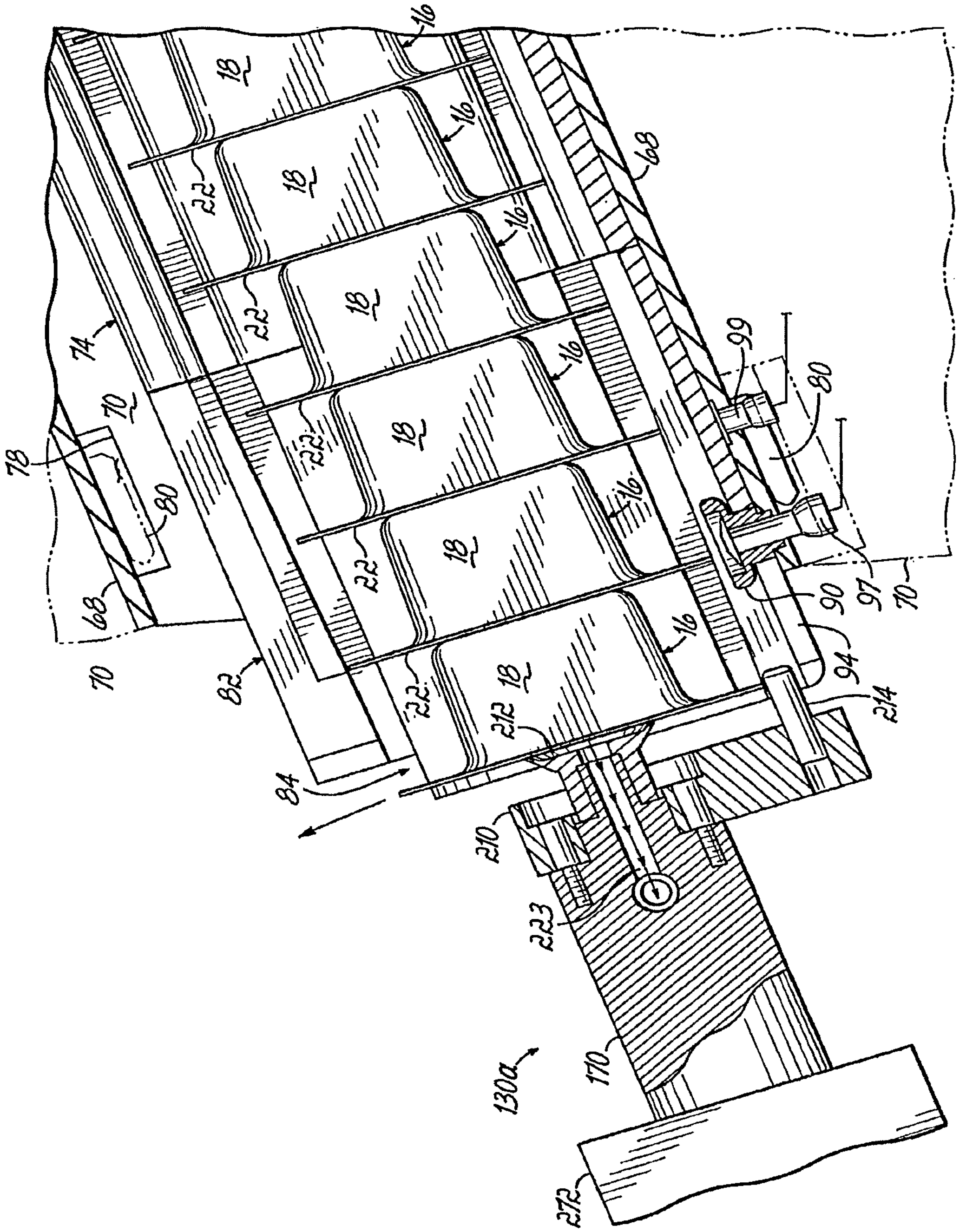
FIG. 12B is an enlarged detail view of the gripper and storage tube of FIG. 12A.
Figure 12C:
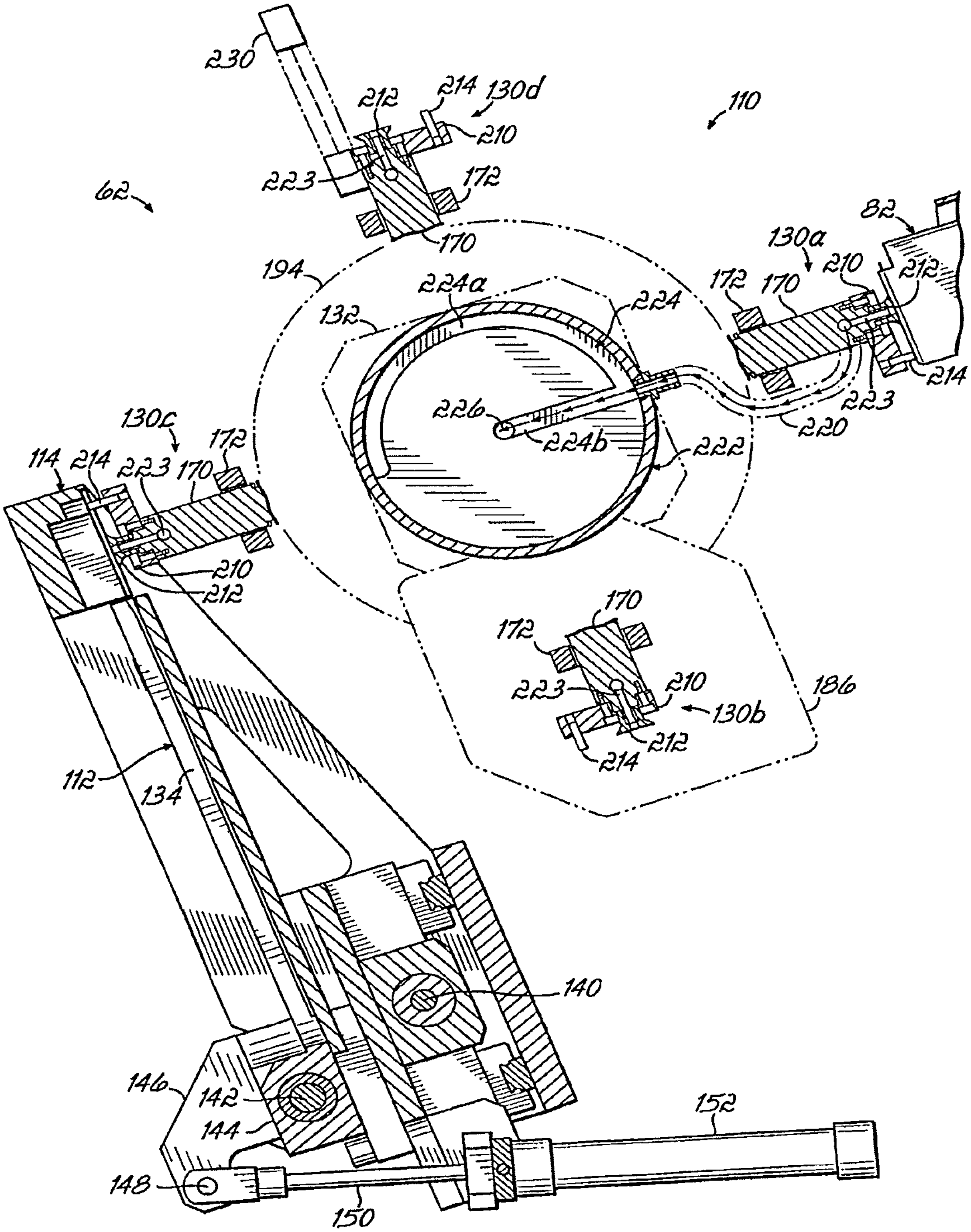
FIG. 12C is a partial cross-sectional view, similar to FIG. 12A, and depicting the vacuum manifold.
Figure 12D:
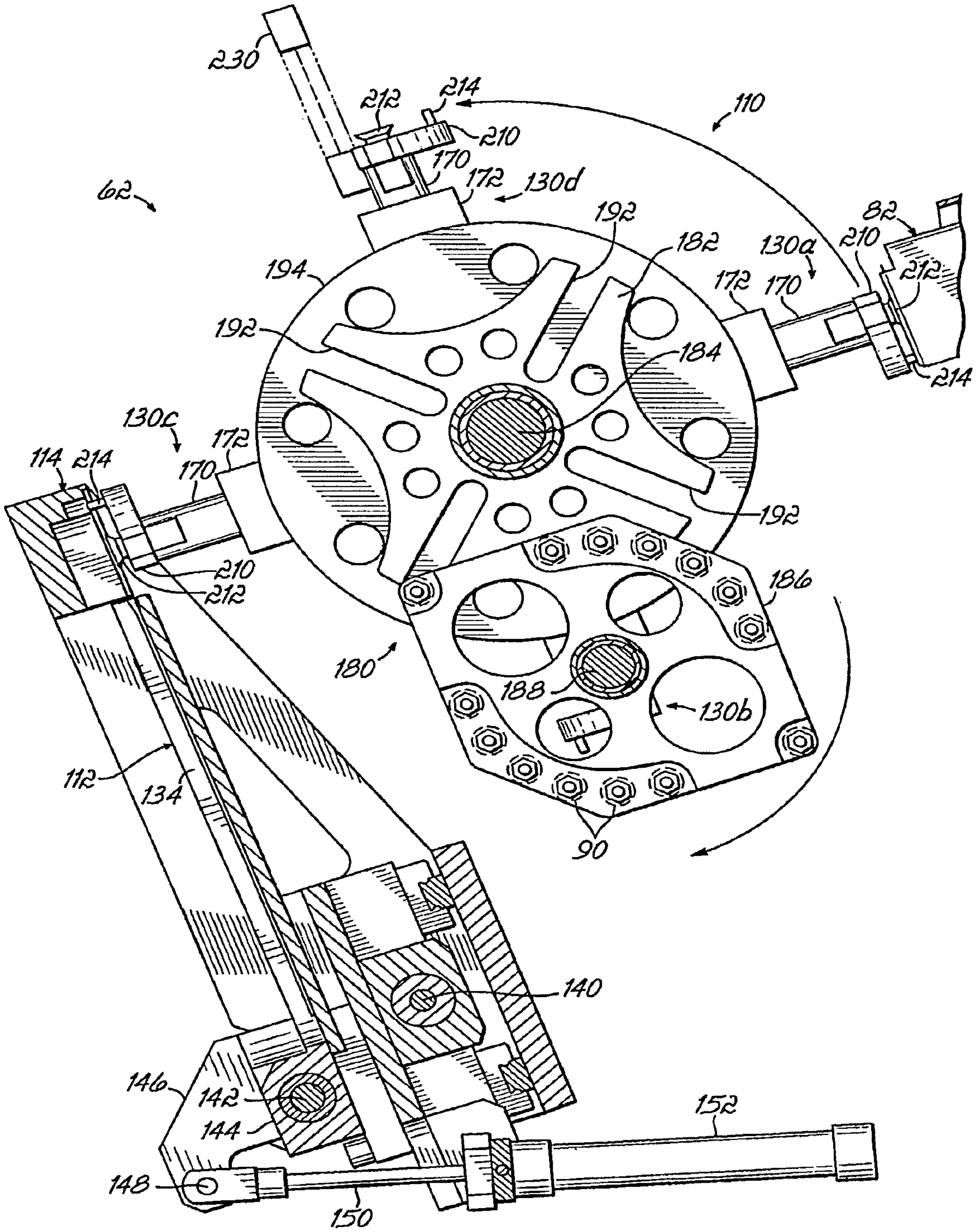
FIG. 12D is a partial cross-sectional view, similar to FIG. 12A, and depicting an indexing mechanism of the pick device.

With continued reference to FIG. 9, and referring further to FIG. 10A, operation of the pick device 62 to retrieve selected packages 16 of medications/supplements from the storage tubes 74 supported in the array of bins 72 of the storage units 66 and to place the selected packages 16 in the transfer nest 112 for subsequent transfer to the transfer station 64 will now be described. The pick device 62 comprises a pick head 110 having four grippers 130 disposed generally circumferentially around a housing 132 of the pick head 110 and arranged such that pairs of grippers 130*a*, 130*c* and 130*b*, 130*d* are positioned on diametrically opposite sides of the housing 132. Each gripper 130 comprises a gripper arm 170 slidably received in guides 172 coupled to the housing 132 to facilitate movement of the gripper arms 170 along radial directions relative to the housing 132. Springs 174 coupled to the gripper arms 170 and contacting the guides 172 bias the gripper arms 170 in directions radially outwardly from the housing 132. The housing 132 of the pick head 110 is rotatable to index the grippers 130 from positions adjacent the storage tubes 74, for engaging and retrieving packages 16 of medications/supplements, to positions adjacent the transfer nest 112 for placing the selected packages 16 into one or more slots 134 of the transfer nest 112. As depicted in FIG. 12D, the pick head 110 of the embodiment shown is rotatably indexed by a Geneva drive mechanism 180 for successive, intermittent positioning of the respective grippers 130 adjacent the storage module 60 and the transfer nest 112. A driven wheel 182 is rotatably supported on a central shaft 184 of the pick head 110 and is driven for intermittent rotation by a drive wheel 186 supported on a rotating drive shaft 188 spaced from the central shaft 184. As the drive wheel 186 rotates, engagement rods 190 positioned on diametrically opposed sides of the drive wheel 186 engage corresponding slots 192 formed in the driven wheel 182 to rotate the driven wheel 182. The driven wheel 182 is coupled to an index plate 194, which is in turn coupled to the pick head housing 132, whereby intermittent rotational motion is imparted to the housing 132 to move the grippers 130.

The pick head 110 is also configured to move the gripper arms 170 along directions extending radially from the housing 132 to facilitate engaging the packages 16 of medications/supplements stored in the storage tubes 74 and placing the selected packages 16 within slots 134 on the transfer nest 112. Radial movement of the gripper arms 170 is controlled by a rotating cam plate 200 disposed within the pick head housing 132. An aperture 202 formed in the cam plate 200 defines a cam surface 204 that engages follower pins 206 coupled to the proximal ends 208 of the gripper arms 170. In the embodiment shown, the cam surface 204 is configured to move one pair of diametrically opposed gripper arms 170 radially outwardly (associated with grippers 130*b* and 130*d*, for example) while the other oppositely disposed pair of gripper arms 170 is moved radially inwardly (associated with grippers 130*a* and 130*c*, for example). The inward/outward motion of the gripper arm pairs is alternated as the cam plate 200 rotates within the pick head housing 132.

Figure 11:
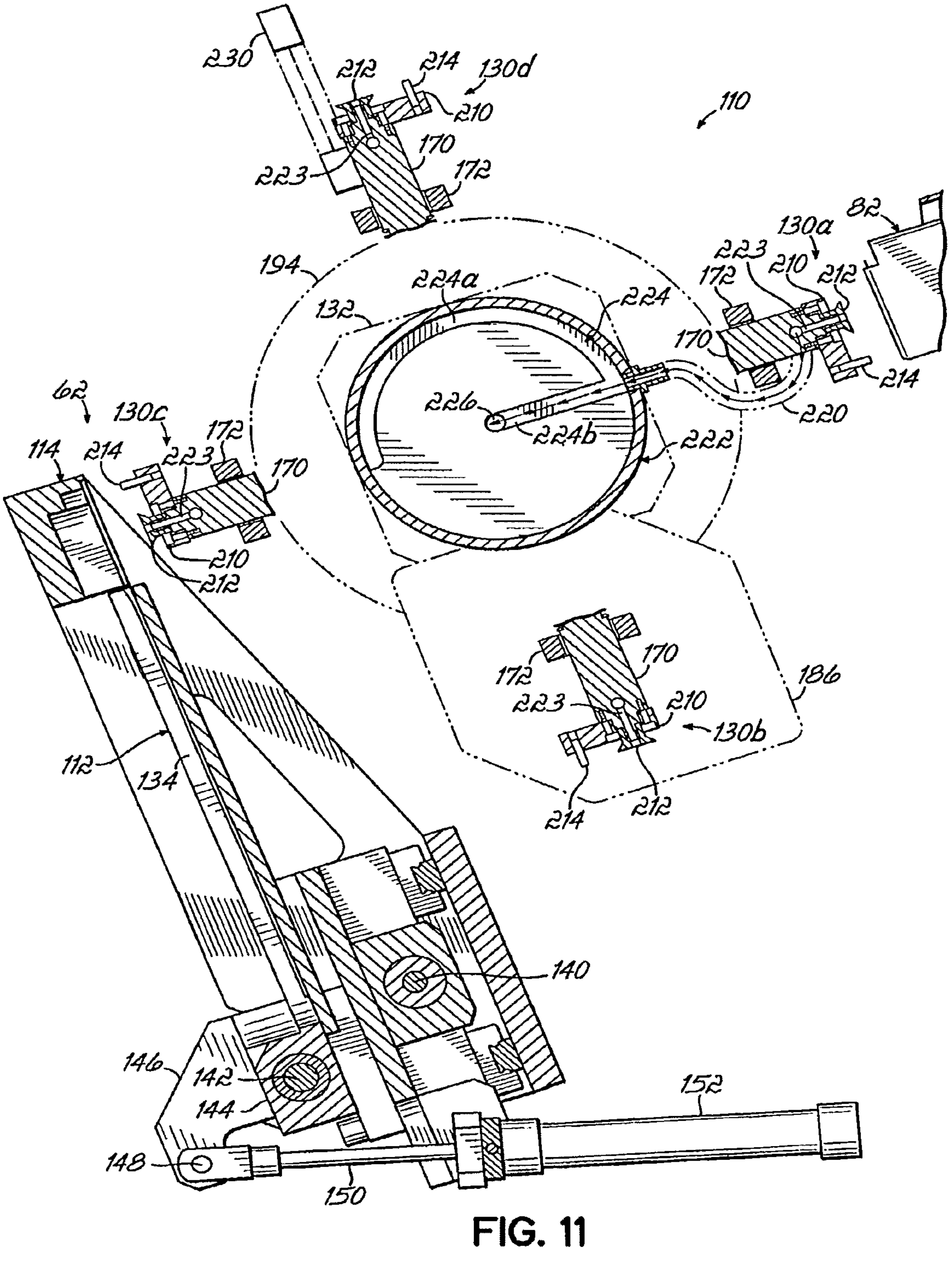
FIG. 11 is a partial cross-sectional view, similar to FIG. 10A, and depicting a vacuum manifold of the pick device.

The distal end 210 of each gripper arm 170 includes a suction cup 212 for applying vacuum pressure to the planar closure 22 of a package 16 positioned adjacent the dispensing slot 84 of a storage tube 74. The distal end 210 of each gripper arm 170 may include a pin 214 for positively engaging an edge of the closure 22 of the package 16 to facilitate lifting the package 16 from the dispensing slot 84 of the storage tube 74. However, the pin 214 may be eliminated to avoid possible damage to the packages 16 during transfer to the slots 134. Vacuum pressure is supplied to the suction cups 212 by conduits 220 that are operatively coupled to a vacuum manifold 222 disposed within the pick head housing 132 and to a vacuum passage 223 in the gripper arm 170. As shown in more detail in FIG. 11, the vacuum manifold 222 comprises a vacuum passage 224 configured to provide vacuum pressure to the suction cups 212 of the respective grippers 130 at appropriate positions of the grippers 130 relative to the pick head housing 134 to facilitate retaining the packages 16 on the distal ends 210 of the gripper arms 170 from the time that the packages 16 are retrieved from the storage tubes 74 until the packages 16 are placed in the slots 134 of the transfer nest 112. To this end, the vacuum passage 224 comprises a first portion 224*a* that extends generally circumferentially around a portion of the pick head housing 132, and a second portion 224*b* extending in a radial direction along the manifold 222 and communicating with an outlet port 226 coupled to a source of vacuum pressure.

With continued reference to FIGS. 10A and 10B, the retrieval of a selected package 16 from a storage tube 74 by the pick head 110 will now be described. In FIG. 10A, the pick head 110 has been moved to a location relative to the storage module 60 to position a first gripper 130*a* adjacent a storage tube 74 supported in the storage module 60 and containing a plurality of packages 16 of a particular medication/supplement required to fill an order. The distal end 210 of the first gripper arm 170 is spaced from the end cap 82 of the storage tube 74. With the first gripper 130*a* positioned adjacent the storage tube 74, vacuum pressure is supplied to the suction cup 212 by the vacuum manifold 222. The cam plate 200 rotates to move the first gripper arm 170 in a direction toward the end cap 82 of the storage tube 74 such that the suction cup 212 engages the surface of the closure 22 of the lower-most package 16 in the storage tube 74, and the pin 214 engages the side edge of the package 16, as depicted in FIGS. 12A and 12B. The vacuum pressure applied at the suction cup 212 draws the package 16 firmly against the distal end 210 of the first gripper 130*a*, and lifts the package 16 through the dispensing slot 84 of the end cap 82 as the Geneva drive mechanism 180 is indexed to the next position, as depicted in FIGS. 12D and 13A.

Figure 13A:
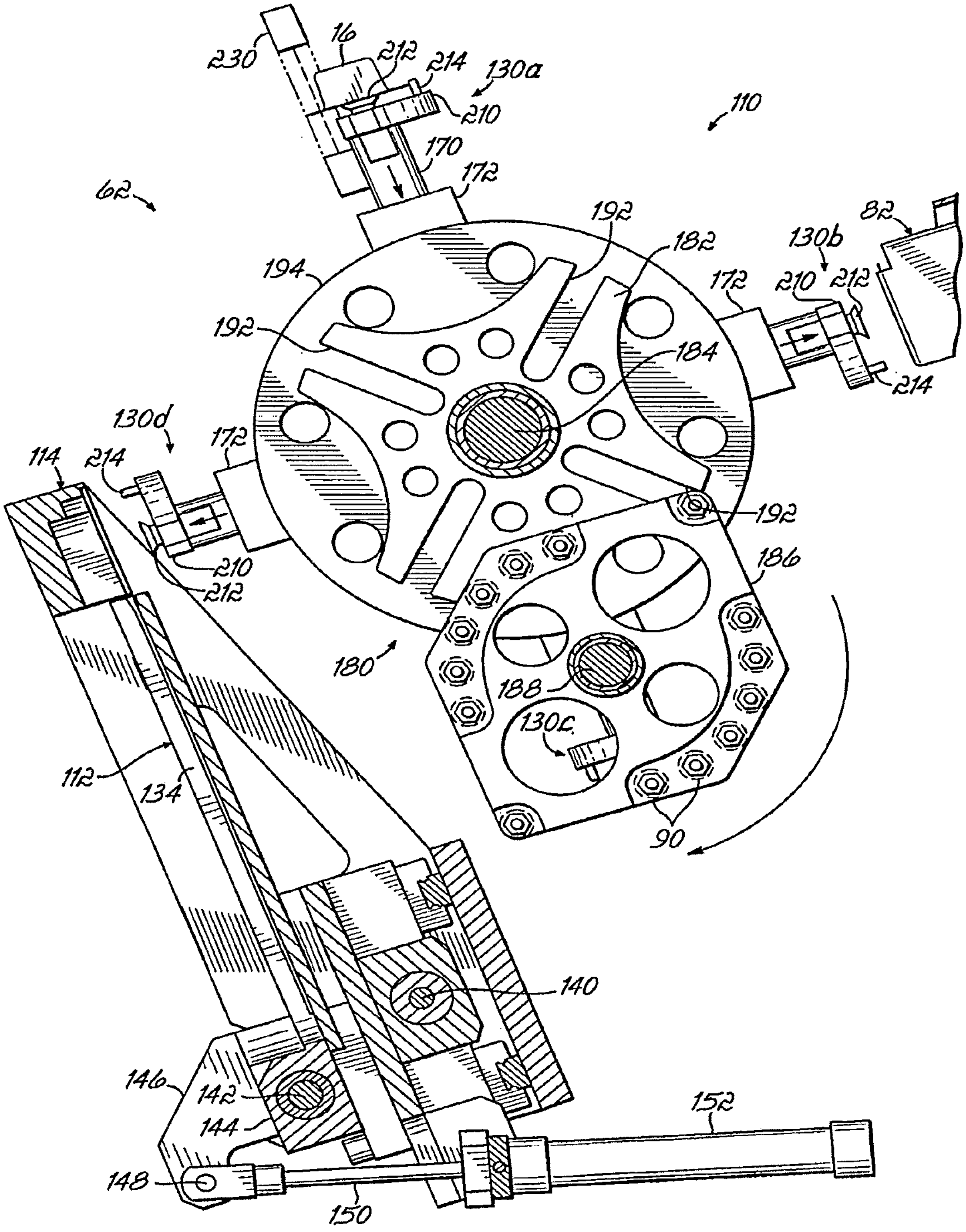
FIG. 13A is a partial cross-sectional view, similar to FIG. 12D, wherein the grippers have been indexed to the next position.
Figure 13B:
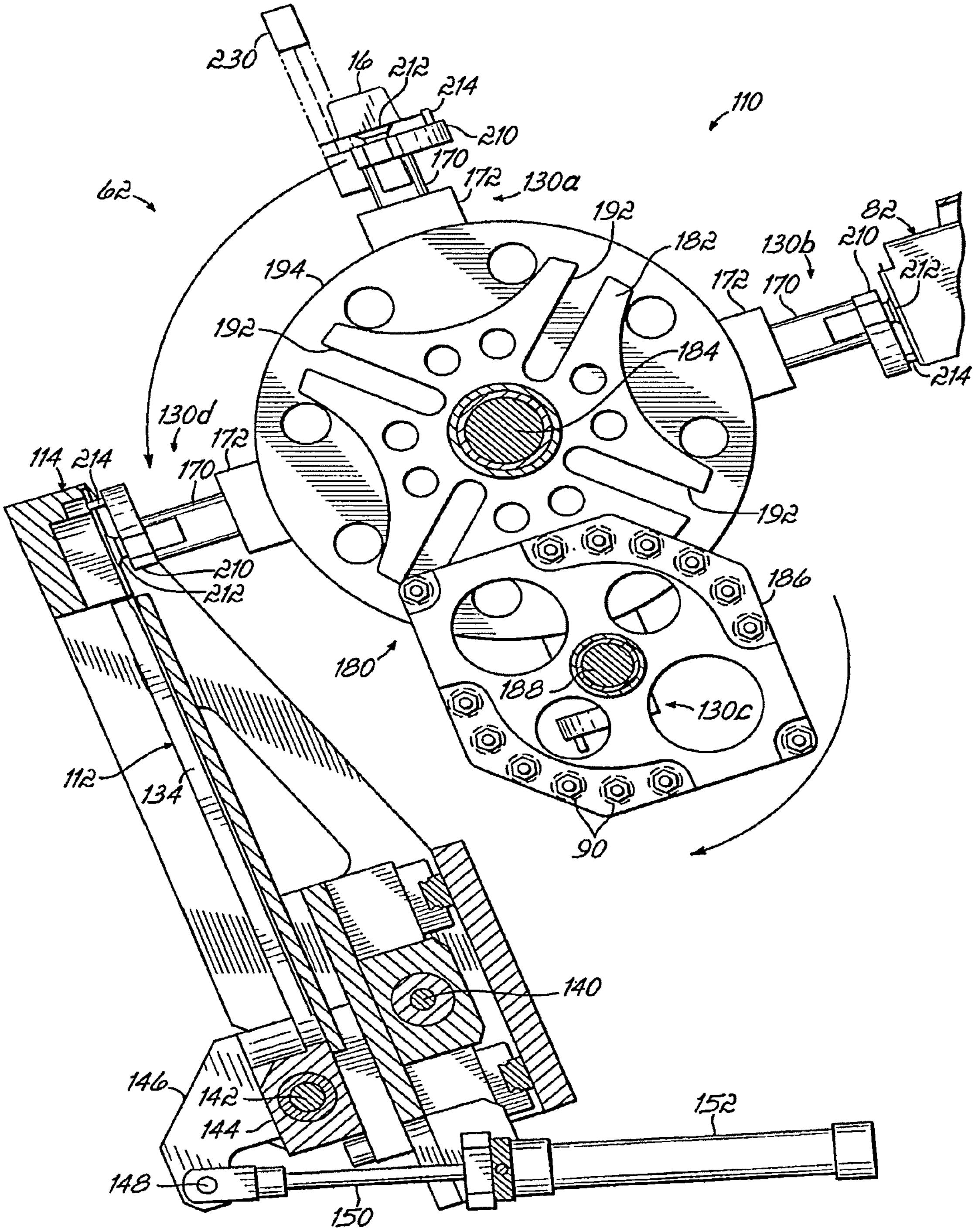
FIG. 13B is a partial cross-sectional view, similar to FIG. 13A, wherein the grippers have been retracted by the cam.

Referring now to FIG. 13A, the selected package 16 is supported on the distal end 210 of the first gripper 130*a* adjacent a sensor 230 configured to detect the presence of a package 16 on the first gripper 130*a*. The sensor 230 may also be configured to read machine readable information provided on the package 16. The sensor 230 can therefore be used to confirm that a package 16 was retrieved by the first gripper 130*a* and that the selected package 16 is the package 16 intended to be selected to fill the order. Indexing of the Geneva drive mechanism 180 to move the first gripper 130*a* and the package 16 supported thereon adjacent the sensor 230 also moves the second gripper 130*b* into a position for engaging and retrieving another package 16 from the storage tube 74, in the event that more than one dose of the medication/supplement is required to fill the order. If a different medication/supplement is required, the pick device 62 may be moved on the gantry 116 to position the second gripper 130*b* adjacent an appropriate storage tube 74 containing packages 16 of the desired medication/supplement.

Figure 13C:
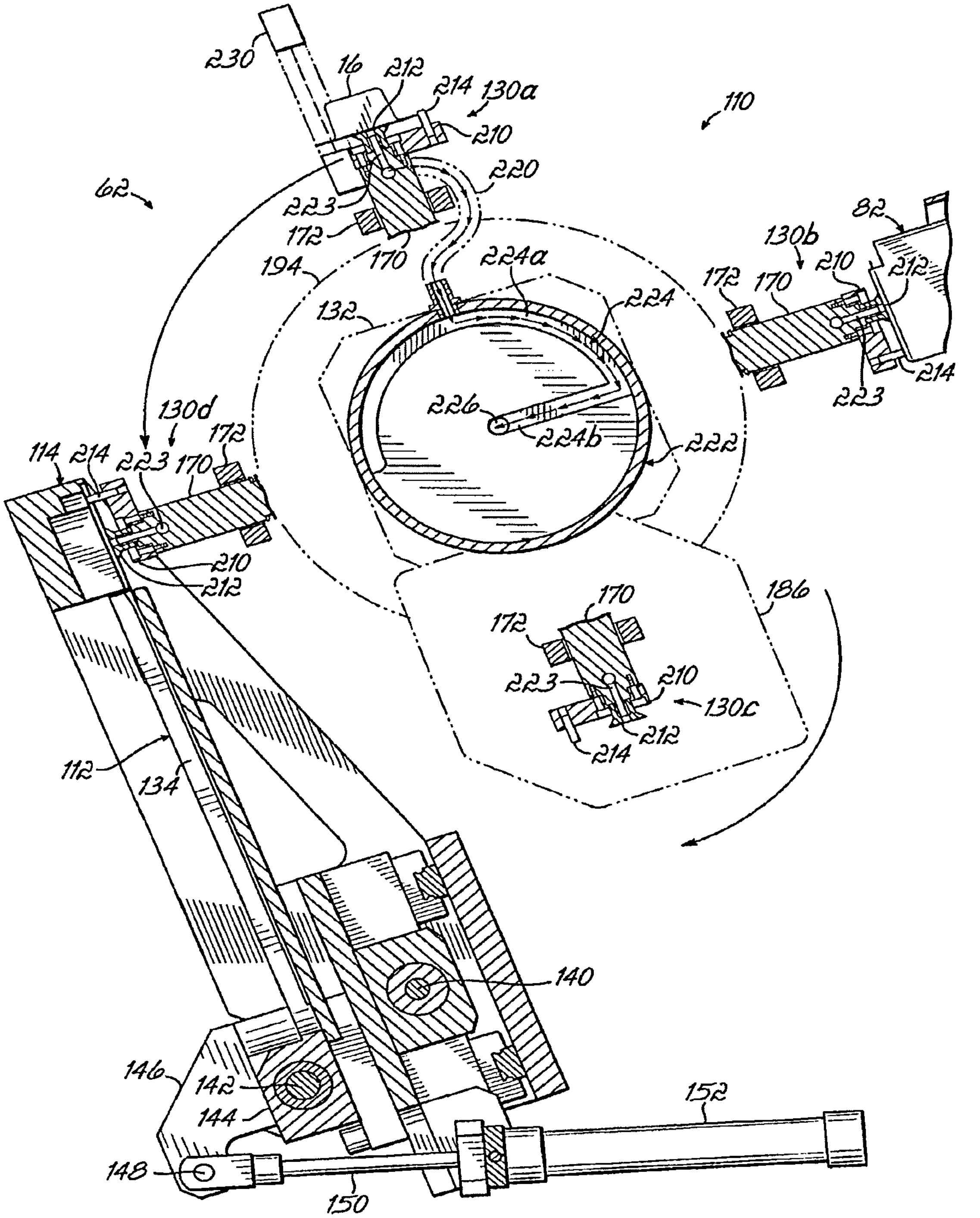
FIG. 13C is a partial cross-sectional top view, similar to FIG. 13B, illustrating the vacuum applied to the grippers.

The cam plate 200 then rotates to move the first gripper 130*a* supporting the package 16 in a direction radially inwardly toward the pick head housing 132, while at the same time the second gripper 130*b* is moved radially outwardly to engage a subsequent package 16 supported in a respective storage tube 74 for retrieval of the package 16 as described above. FIG. 13C depicts the vacuum manifold 222 and illustrates how vacuum pressure is maintained at the suction cup 212 of the first gripper 130*a* adjacent the sensors 230.

Figure 14A:
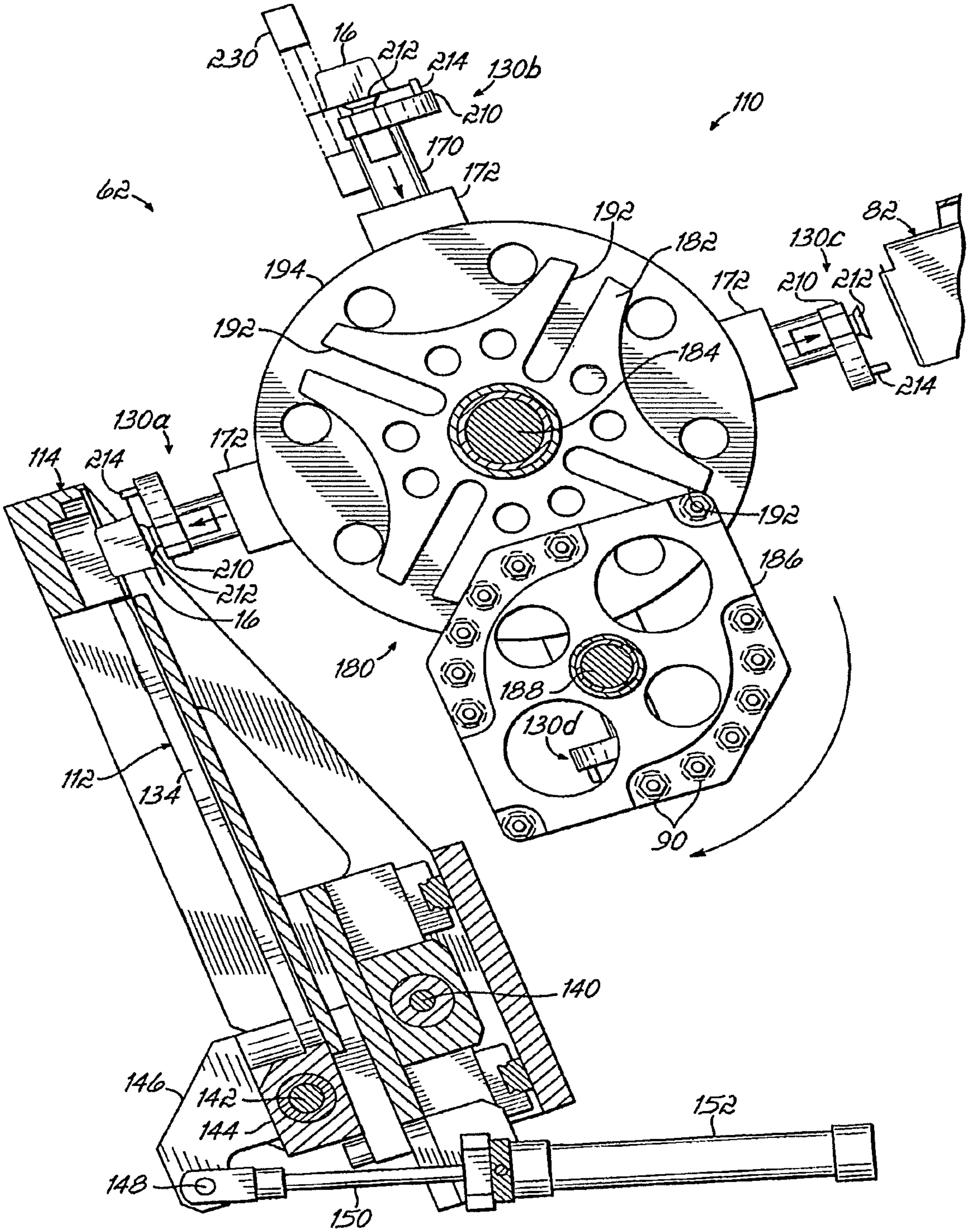
FIG. 14A is a partial cross-sectional view, similar to FIG. 13B, wherein the grippers are indexed to a successive position.
Figure 14B:
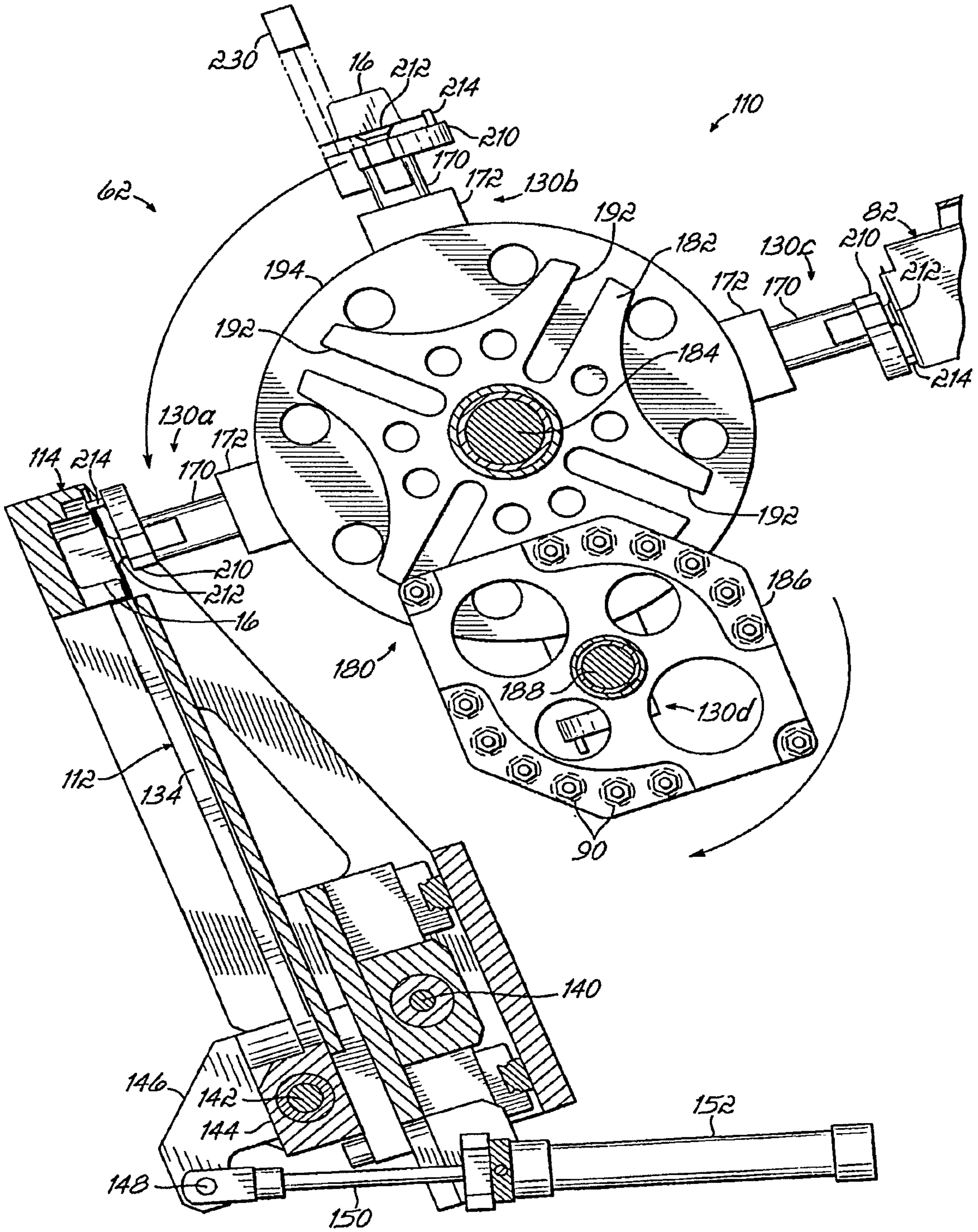
FIG. 14B is a partial cross-sectional view, similar to FIG. 14A, depicting the grippers extended and retracted by the cam.
Figure 14C:
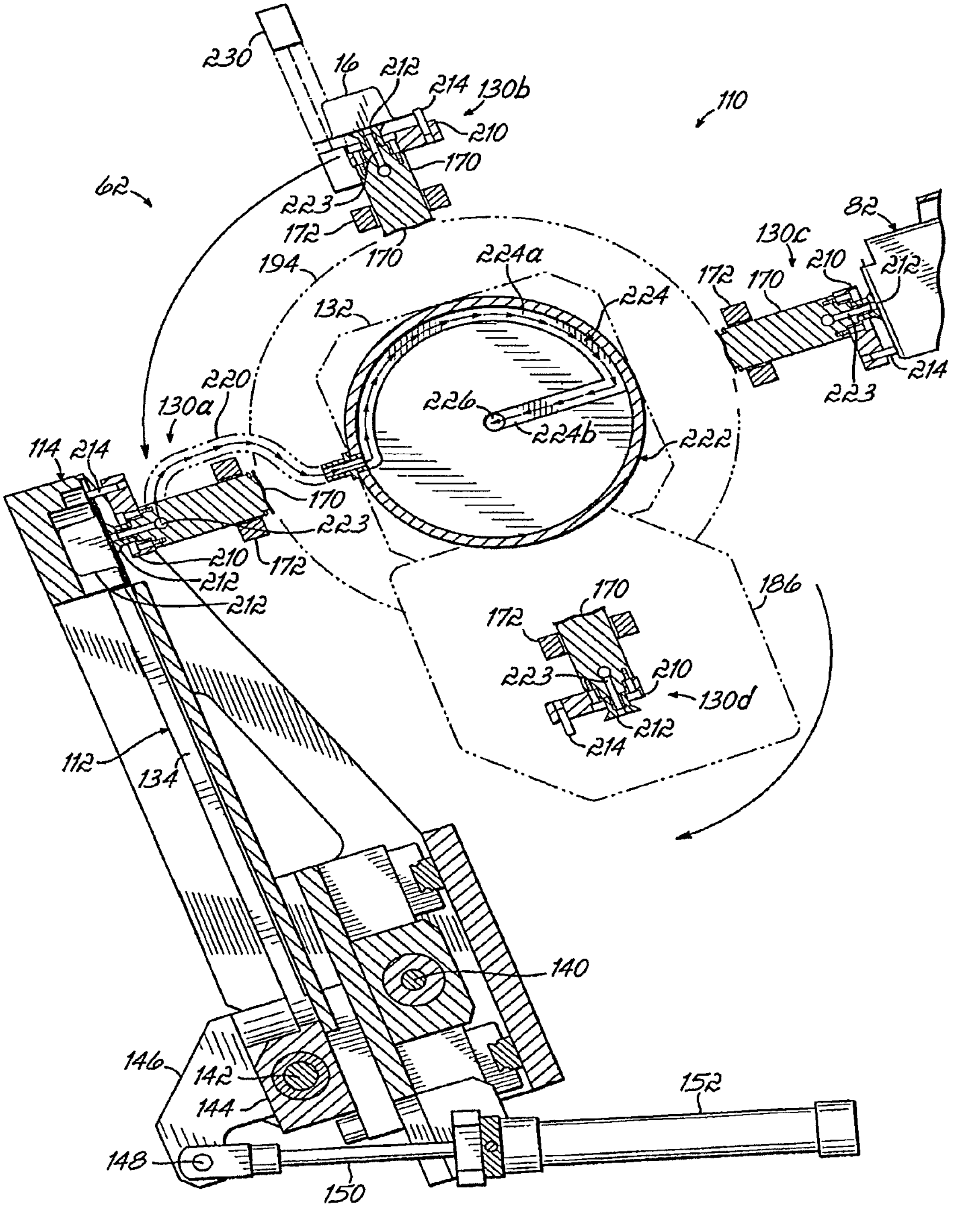
FIG. 14C is a partial cross-sectional view, similar to FIG. 14B, illustrating the vacuum pressure applied to the grippers.
Figure 15:
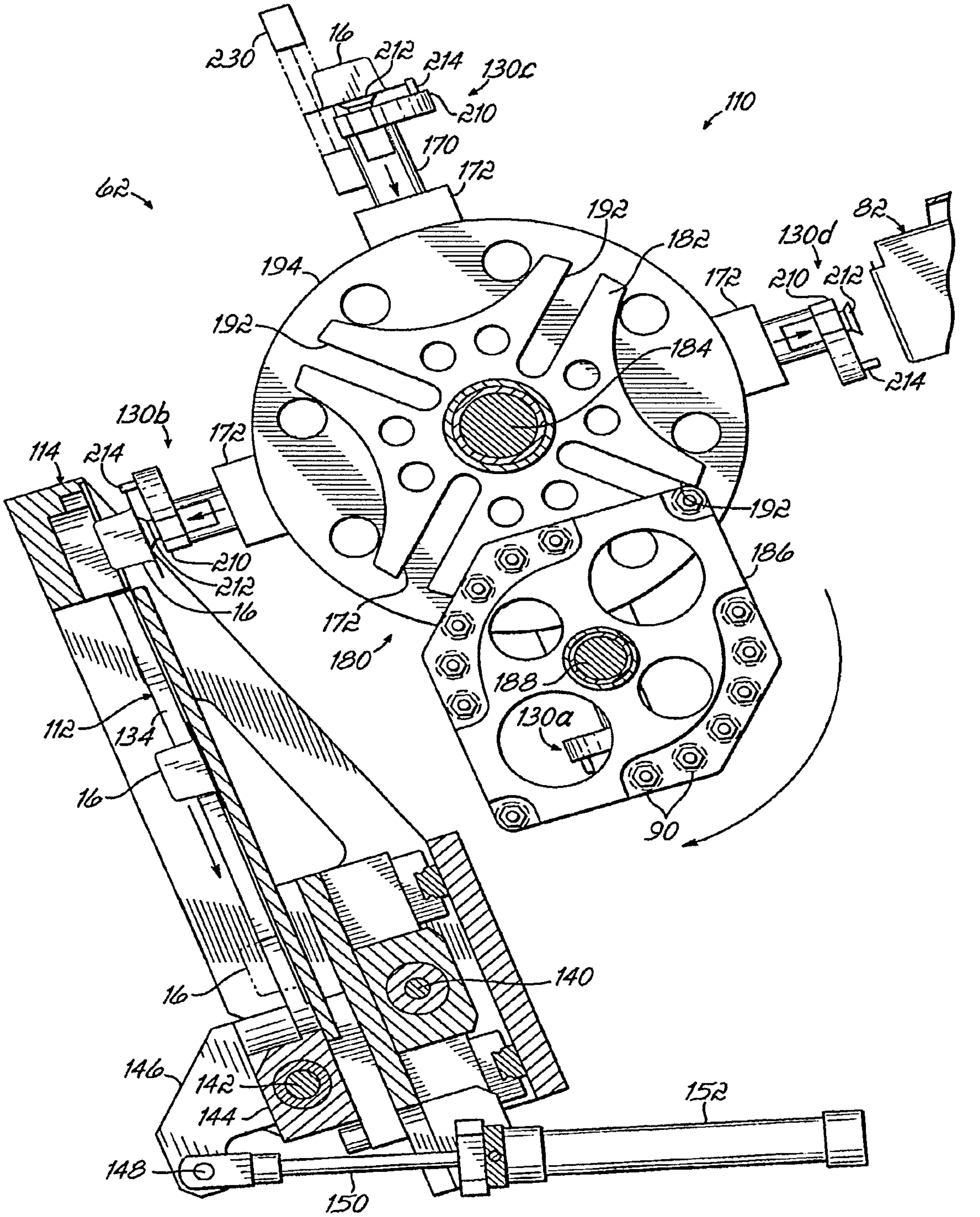
FIG. 15 is a partial cross-sectional view, similar to FIG. 14B, depicting the grippers of the pick device indexed to the next position.

Referring now to FIG. 14A, the Geneva drive mechanism 180 indexes the first gripper 130*a* to a position adjacent the transfer nest 112, while simultaneously moving the second gripper 130*b* (now supporting a package 16) adjacent the sensor 230, and moving the third gripper 130*c* adjacent the storage module 60 to a position to retrieve a subsequent package 16 from the same storage tube 74, or from a different storage tube 74, as may be required. As the drive wheel 186 of the Geneva drive mechanism 180 continues to rotate, the cam plate 200 rotates to move the first gripper 130*a* radially outwardly to position the package 16 in registration with a selected slot 134 of the transfer nest 112, as depicted in FIG. 14B. Simultaneously, the second gripper 130*b* is moved in a direction radially inwardly, while the third gripper 130*c* is moved radially outwardly to engage a subsequent package 16. FIG. 14C illustrates the vacuum manifold 222 with the first gripper 130*a* adjacent the transfer nest 112 and shows how vacuum pressure is applied to the suction cup 212 at this position. As the first gripper 130*a* is subsequently indexed to the next position, vacuum pressure applied through the first portion 224*a* of the vacuum passage 224 is shut off to the conduit 220, and the package 16 is released into the slot 134 on the transfer nest 112, as illustrated in FIG. 15, which depicts the pick head 110 indexed to the next successive position by the Geneva drive mechanism 180, whereby the second gripper 130*b* is in position to place a package 16 supported on the second gripper 130*b* onto the transfer nest 112. After the last package 16 in an order is picked, the Gantry 116 moves the pick device 62 to a location between the storage units 66, where there are no storage tubes 74. Since there are no packages 16 present, the pick device 62 can advance two positions thereby transferring the packages already supported by the remaining two grippers 130 into the slot 134 of the transfer nest 112 without acquiring additional packages 16, completing the order.

Figure 16:
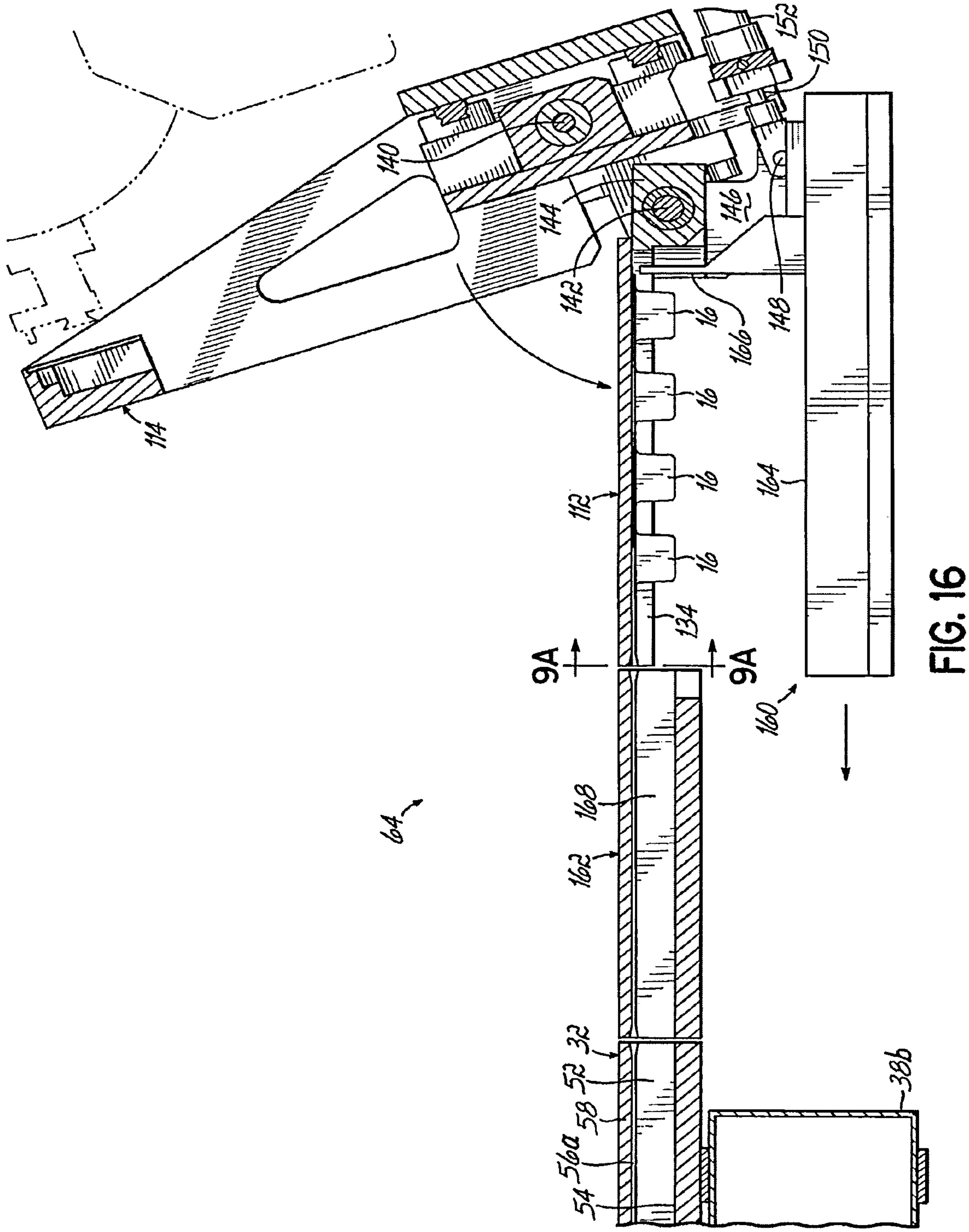
FIG. 16 is a partial cross-sectional view depicting the transfer of packages from the transfer nest to the transfer station.
Figure 17:
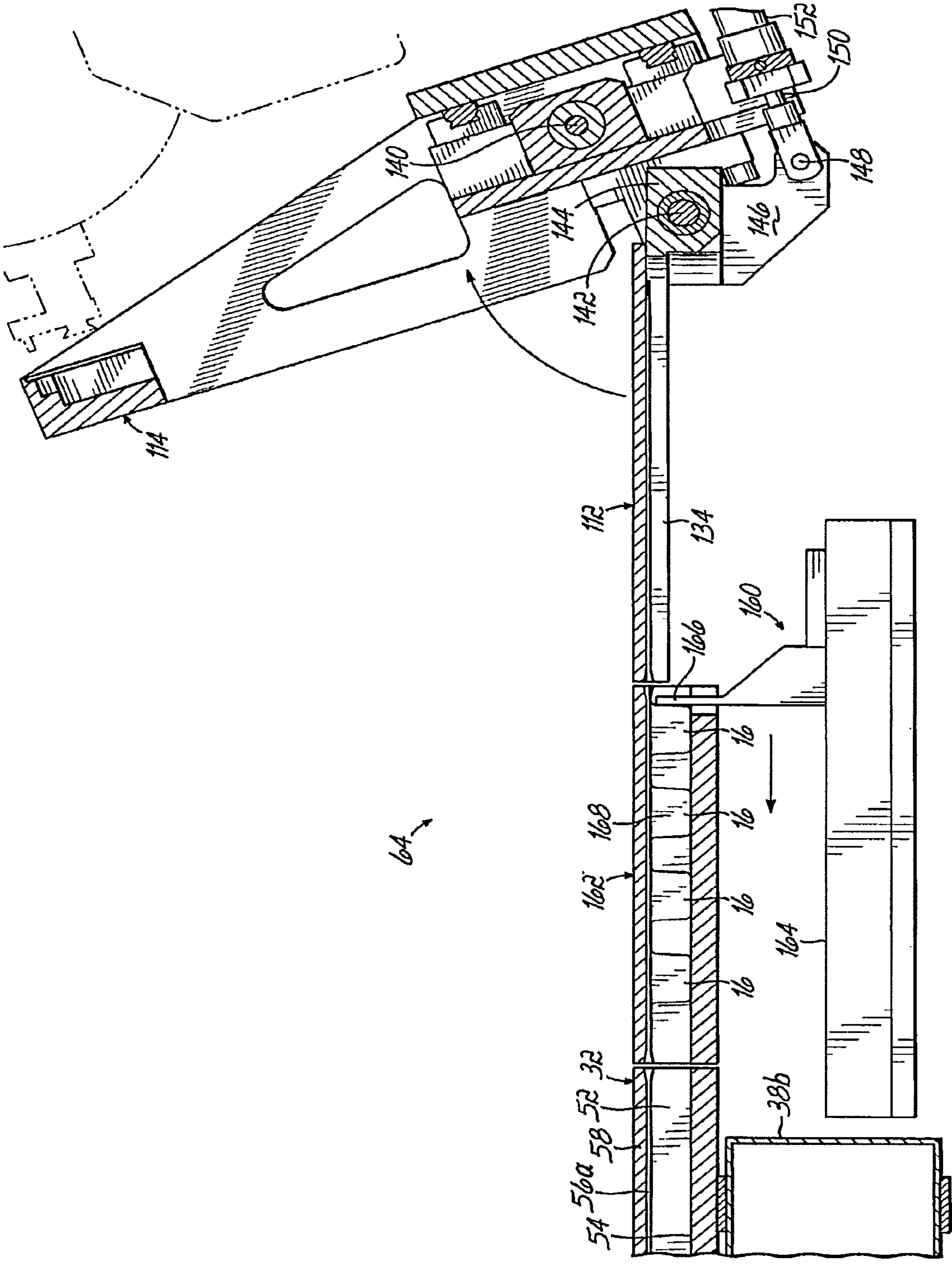
FIG. 17 is a partial cross-sectional view, similar to FIG. 16, depicting the packages in the queue support of the transfer station.
Figure 18:
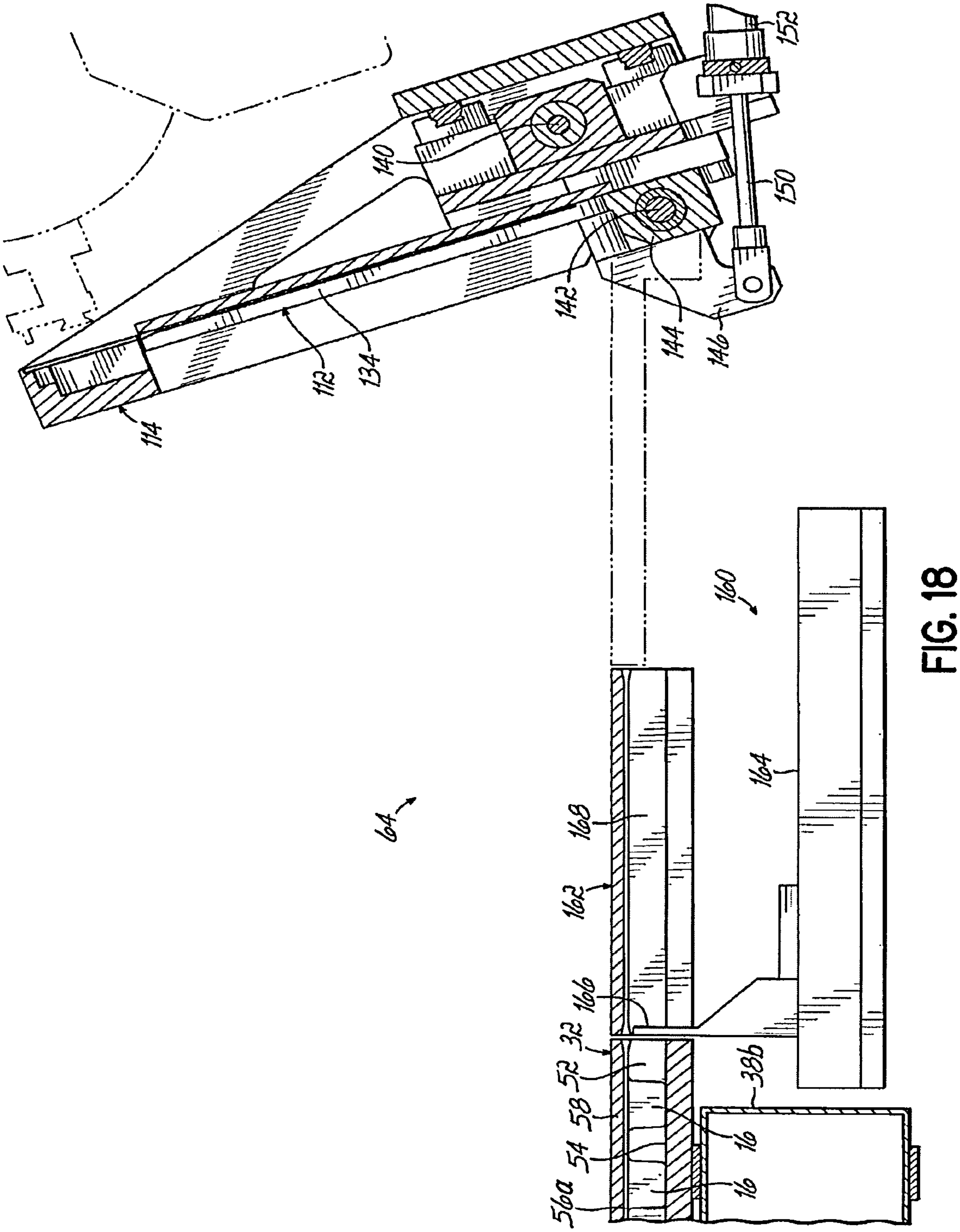
FIG. 18 is a partial cross-sectional view, similar to FIG. 17, depicting the packages transferred between the queue support and a carrier on the conveyor.

After the packages 16 of medications/supplements associated with one or more orders are placed on the transfer nest 112, the pick device 62 is moved by the gantry 116 to a position adjacent the transfer station 64. The pneumatic cylinder 152 is then actuated to pivot the transfer nest 112 from the first position adjacent the pick head 110 to the second position adjacent the slide assembly 160 of the transfer station 64, as depicted in FIG. 16. With the transfer nest 112 in the second position, one or more of the slide members 164 may be actuated to push the selected packages 16 from the slots 134 on the transfer nest 112 into corresponding channels 168 on the queue support 162 in registration with the slots 134 of the transfer nest 112, as depicted in FIG. 17. The packages 16 of medications/supplements supported in the queue support 162 are held until the designated carrier 32 assigned to receive the particular order associated with the medications/supplements is in position adjacent the corresponding channel 168 of the queue support 162. Thereafter, the prongs 166 of the slide member 164 are further actuated to push the corresponding packages 16 of medications/supplements from the queue support 162 into the appropriate carrier 32 on the conveyor 30, as depicted in FIG. 18.

After the packages 16 of medications/supplements have been moved from the transfer nest 112 to the slide assembly 160, the transfer nest 112 is pivoted from the second position back to the first position, adjacent the pick head 110, and the pick device 62 is moved on the gantry 116 to a position adjacent a selected storage tube 74 for retrieval of a package 16 required for the next order. The process described above is repeated to assemble additional orders. After the packages 16 of medications/supplements for an order have been transferred from the queue support 162 to the assigned carrier or carriers 32, the slide members 164 return to retracted positions as depicted in FIG. 16 to await the delivery of the next batch of packages 16 from the pick device 62. Having received all of the packages 16 of medications/supplements required to fill the orders, the carriers 32 continue along the conveyor 30 to a packaging station for subsequent processing into appropriate containers for delivery to the one or more long-term care facilities.

In the embodiment shown, the low-demand module 14 of the dispensing system 10 includes five individual transfer stations 64 configured to receive packages 16 of medications/supplements for transfer to respectively assigned carriers 32 on the conveyor 30, as described above. it will be appreciated, however, that the dispensing system may alternatively include fewer than five transfer stations 64, or greater than five transfer stations 64, as may be desired for the particular requirements of the dispensing system 10. The provision of multiple transfer stations 64 enables the pick head 110 to preselect the packages 16 of medications/supplements associated with a plurality of orders and transfer the packages 16 into respective queue supports 162 to accommodate substantially continuous operation of the conveyor 30. In one embodiment, the conveyor 30 is configured to incrementally move the carriers 32 from the first end 34 to the second end 36 such that a carrier 32 is indexed approximately every 3 seconds.

The dispensing system 10 further includes a control 240 configured to receive orders for medications/supplements and to process the orders for delivery to a long-term care facility. Orders may be electronically received by the control 240 from one or more long-term care facilities, such as by transmission over a network, or by any other suitable method. Alternatively, orders can be input directly into the control 240 via an appropriate interface, such as a keyboard or other suitable devices. The control 240 identifies which medications/supplements are required from the high-demand module 12 and the low-demand module 14 to fill each order. In one embodiment, the orders corresponding to each medication pass to be administered to a particular patient for that particular day are processed by the control 240 such that the packages 16 of medications/supplements for each medication pass to be administered to the patient are assembled into a package, and the packages of medication passes are then grouped together for delivery to the long-term care facility.

The control 240 assigns one or more carriers 32 to receive the packages 16 of medications/supplements for each order. The control 240 then controls the movement of the carriers 32 on conveyor 30 through the high-demand module 12 and the low-demand module 14 to receive the packages 16 as described above and in related U.S. patent application Ser. No. 12/559,630, filed on even date herewith and incorporated herein in its entirety. The control 240 controls operation of the low-demand module 14 to retrieve the packages 16 of medications/supplements for the orders ahead of the arrival of the carriers 32 assigned to the orders and while the carriers 32 are receiving the ordered medications/supplements from the high-demand module 12 as the carriers 32 are moved past the high-demand module 12. The transfer nests 64 provide a buffer to accumulate the medications/supplements in advance of the arrival of the carrier 32 for the specific order. The control 240 is coupled to an order entry database and via a web service the orders are passed to the dispenser 10 one at a time. Alternatively, multiple orders may be passed at a time, for example, ten orders passed at a time. As such, the remaining, subsequent orders are buffered in the database.

In another embodiment, the dispensing system 10 may be configured to receive and process short turn-around time orders ("stat orders") that are received separately from the periodically received orders from the long-term care facilities. The control 240 integrates the stat orders into the orders being processed and may direct the assembled stat order to a separate location for subsequent handling.

The control 240 may also be configured to receive signals from various sensors associated with the dispensing system 10 to facilitate managing operation of the dispensing system 10. For example, in one embodiment, the control 240 is configured to receive signals from sensors 97, 99, 230 of the low-demand module 14 related to the detection of packages 16 in a storage tube 74, the presence of storage tubes 74 in a bin 72, and the presence of a package 16 supported on a gripper 130, respectively. When the control 240 receives a signal from a sensor 97 indicating that the storage tube 74 associated with the sensor 97 is empty, control 240 provides a signal to an operator indicating that the storage tube needs to be replaced or replenished. When control 240 receives a signal from a sensor 99 indicating that a storage tube 74 is not detected in the associated bin 72, the control may provide a signal to an operator indicating the detected absence of a storage tube 74. Inventory status is maintained in the control 240 and the sensor 230 provides a fail-safe check in case the inventory is not correct in that the control 240 will not direct the pick device 62 to pick from an empty location. When control 240 receives a signal from a sensor 230 indicating that a package 16 was not detected on a gripper 130, the control may provide a signal to an operator that the package 16 was not detected. The control 240 may also flag the order associated with the detected absence of the package 16 for separate processing to confirm that the order is faulty and, optionally, to correct the error in filling the order. The control 240 may also be configured to stop operation of the dispensing system 10 when a detected error will adversely affect operation of the dispensing system 10 to fill orders.

The control 240 may also be configured to optimize the picking of packages 16 from the storage module 60 and the transfer of the packages 16 to the carriers 32. In particular, the control 240 may be configured to monitor the order frequency of the medications/supplements and to assign locations for the storage tubes 74 in the bins 72 of the storage module 60 based on order frequency. For example, the control 240 may assign locations for storage tubes 74 containing medications/supplements that have a relatively higher order frequency to be placed in bins 72 that are located relatively lower in the storage units 66 and/or are positioned relatively closer to the transfer stations 64 so that the distance required to be traversed by the pick device 62 to retrieve packages 16 of high demand medications/supplements is minimized, thereby decreasing the time required to transfer packages 16 for the orders in the queue supports 162. Accordingly, the particular locations of the storage tubes 74 within the bins 72 of the storage module 60 can be dynamic and may be modified by the control 240, as may be desired for efficient processing of orders.

In another embodiment, the control 240 may be configured to track the dispensing of medications/supplements from the storage tubes 74 within the storage module and to provide signals to an operator when the supply of packages 16 in a given storage tube 74 is becoming low. This allows replacement of the storage tubes 74 or, alternatively, replenishment of the packages 16 within the storage tubes 74, at convenient times. The dispensing system 10 is also configured to facilitate replacement of the storage tubes 74 or, alternatively, replenishment of the packages 16 within the storage tubes 74, on-the-fly while the dispensing system 10 is operating to fill orders. In particular, the configuration of the storage module 60 facilitates access to the receiving ends 76 of the bins 72 for removal and replacement of storage tubes 74 while the dispensing system is operating to fill orders. In the event that the pick device 62 attempts to retrieve a package 16 from a storage tube 74 when the storage tube 74 has been removed for replacement, the control 240 receives a signal from sensor 99 associated with the bin 72 and may control the pick device 62 to wait until the storage tube 74 has been replaced before attempting to retrieve the package 16.

While FIG. 1 illustrates the dispensing system 10 as having a high-demand module 12 and a low demand module 14 provided on only one side of the conveyor 30, the dispensing system 10 may alternatively be configured with high-demand modules 12 and low-demand modules 14 provided on both sides of the conveyor 30, to accommodate the quantity of medications/supplements and throughput requirements of the system, as may be desired. In such a configuration, the high-demand modules 12 and low demand modules 14 on both sides of the conveyor 30 are controlled by a common controller 240 and operate generally as described above and in U.S. patent application Ser. No. 12/559,630, however, the packages 16 of medications/supplements may be transferred to the carriers 32 moving along the conveyor 32 from the high-demand modules 12 and low-demand modules 14 on both sides of the conveyor 30.

While the present invention has been illustrated by the description of one or more embodiments thereof, and while the embodiments have been described in considerable detail, they are not intended to restrict or in any way limit the scope of the appended claims to such detail. The various features described herein may be utilized alone or in any combination. Additional advantages and modifications will readily appear to those skilled in the art. The invention in its broader aspects is therefore not limited to the specific details, representative apparatus and method and illustrative examples shown and described. Accordingly, departures may be made from such details without departing from the scope or spirit of the general inventive concept.

The invention claimed is:

1. An automation apparatus for dispensing groups of individually packaged products, the apparatus comprising:

a storage module including a first storage bin, the first storage bin being defined by a first vertical wall, a second vertical wall opposite the first vertical wall, and a floor, the first storage bin configured to slidably receive a storage tube inserted therein;

a first storage tube including a hollow body configured to store therein a plurality of products each contained in an individual package, the first storage tube including an end cap attached at a dispensing end of the first storage tube, the end cap including a release slot along an upwardly facing side of the storage tube to allow movement of a first individual package along a direction transverse to a longitudinal axis of the first storage tube for removal of the first individual package from the storage tube, the end cap including a retention slot disposed along a floor of the end cap configured to engage with a registration pin disposed along the floor of the first storage bin and prevent the first storage tube from sliding out of the first storage bin; and a pick device movable vertically and horizontally to traverse the storage module and the first storage bin at the dispensing end of the first storage tube, the pick device configured to retrieve the first individual package from the first storage tube disposed in the end cap, the pick device configured to contact the first individual package and translate the first individual package along the direction transverse to the longitudinal axis of the first storage tube to remove the first individual package from the first storage tube.

* * * * *